(12) United States Patent
Lin et al.

(10) Patent No.: US 6,495,100 B1
(45) Date of Patent: Dec. 17, 2002

(54) METHOD FOR STERILIZING DEVICES IN A CONTAINER

(75) Inventors: Szu-Min Lin, Laguna Hills, CA (US); Anthony Lemus, Yorba Linda, CA (US); Harold R. Williams, San Clemente, CA (US); Paul Taylor Jacobs, Trabuco Canyon, CA (US); Tralance O. Addy, Coto de Caza, CA (US); Jon Morrell Jacobs, Trabuco Canyon, CA (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 09/470,244

(22) Filed: Dec. 22, 1999

Related U.S. Application Data

(63) Continuation-in-part of application No. 09/105,280, filed on Jun. 26, 1998, now Pat. No. 6,068,817, which is a division of application No. 08/833,375, filed on Apr. 4, 1997, now Pat. No. 5,961,921, which is a continuation-in-part of application No. 08/628,965, filed on Apr. 4, 1996.

(51) Int. Cl.⁷ ................................................. A61L 2/20
(52) U.S. Cl. .......................................... 422/29; 422/33
(58) Field of Search ........................... 422/29, 33, 292, 422/300

(56) References Cited

U.S. PATENT DOCUMENTS

| 4,169,123 A | 9/1979 | Moore et al. |
|---|---|---|
| 4,169,124 A | 9/1979 | Forstrom et al. |
| 4,230,663 A | 10/1980 | Forstrom et al. |
| 4,643,876 A | 2/1987 | Jacobs et al. |
| 4,756,882 A | 7/1988 | Jacobs et al. |
| 4,909,999 A | 3/1990 | Cummings et al. |
| 4,943,414 A | 7/1990 | Jacobs et al. |
| 4,952,370 A | 8/1990 | Cummings et al. |
| 4,956,145 A | 9/1990 | Cummings et al. |
| 5,087,418 A | 2/1992 | Jacob |
| 5,115,166 A | 5/1992 | Campbell et al. |
| 5,286,448 A | 2/1994 | Childers et al. |
| 5,310,524 A | 5/1994 | Campbell et al. |

(List continued on next page.)

FOREIGN PATENT DOCUMENTS

| CA | 214 9923 | 6/1994 |
|---|---|---|
| DE | 26 23 917 A1 | 12/1977 |
| DE | 41 02 055 A1 | 8/1991 |
| EP | 0 223 479 A2 | 5/1987 |
| EP | 0 302 419 B1 | 2/1989 |

(List continued on next page.)

*Primary Examiner*—Elizabeth McKane
(74) *Attorney, Agent, or Firm*—Knobbe, Martens, Olson & Bear, LLP

(57) ABSTRACT

A method for sterilizing medical devices and similar instruments in diffusion-restricted containers is provided. The sterilization method includes placing a liquid solution containing vaporizable germicide such as hydrogen peroxide into the diffusion-restricted container and vaporizing the germicide. The containers can be attachable and detachable to a sterilization system, and used as a vacuum chamber. An attachable/detachable container containing an article to be sterilized can be nested with a second container, and the article and inside and outside of the inner container are sterilized. The sterile article inside the nested containers can be transported and the sterile inner container with the sterilized article can removed from the outer container and placed in a sterile environment without contaminating the sterile environment. The sterile article can then be removed from the sterile container and utilized. Alternatively, the sterilization method may include introducing germicide vapor into an attachable/detachable container.

33 Claims, 20 Drawing Sheets

U.S. PATENT DOCUMENTS

| | | |
|---|---|---|
| 5,346,075 A | 9/1994 | Nichols et al. |
| 5,413,758 A | 5/1995 | Caputo et al. |
| 5,413,760 A | 5/1995 | Campbell et al. |
| 5,443,801 A | 8/1995 | Langford |
| 5,451,368 A | 9/1995 | Jacob |
| 5,492,672 A | 2/1996 | Childers et al. |
| 5,527,508 A | 6/1996 | Childers et al. |
| 5,534,221 A | 7/1996 | Hillebrenner et al. |
| 5,556,607 A | 9/1996 | Childers et al. |
| 5,580,530 A | 12/1996 | Kowatsch et al. |
| 5,633,424 A | 5/1997 | Graves et al. |
| 5,656,238 A | 8/1997 | Spencer et al. |
| 5,667,753 A | 9/1997 | Jacobs et al. |
| 5,770,739 A | 6/1998 | Lin et al. |
| 5,792,422 A | 8/1998 | Lin et al. |
| 6,013,227 A | 1/2000 | Lin et al. |
| 6,015,529 A | 1/2000 | Lin et al. |

FOREIGN PATENT DOCUMENTS

| | | |
|---|---|---|
| EP | 0 207 417 B1 | 9/1990 |
| EP | 0 456 135 A2 | 11/1991 |

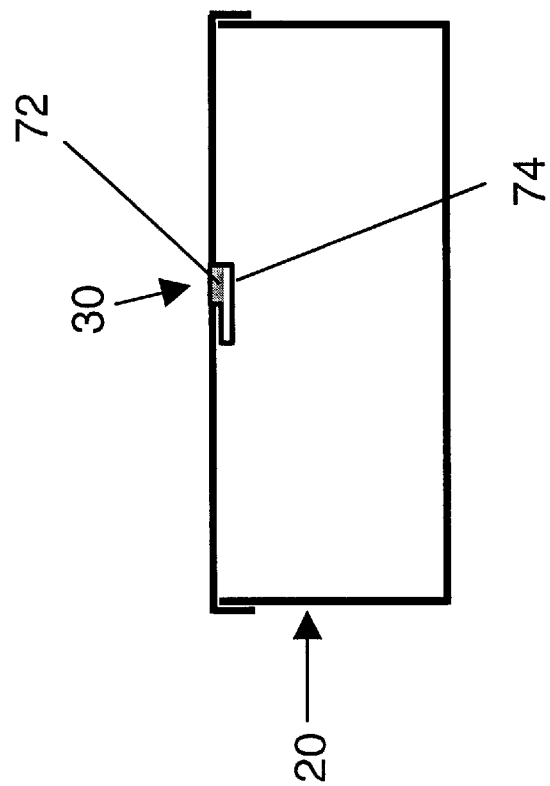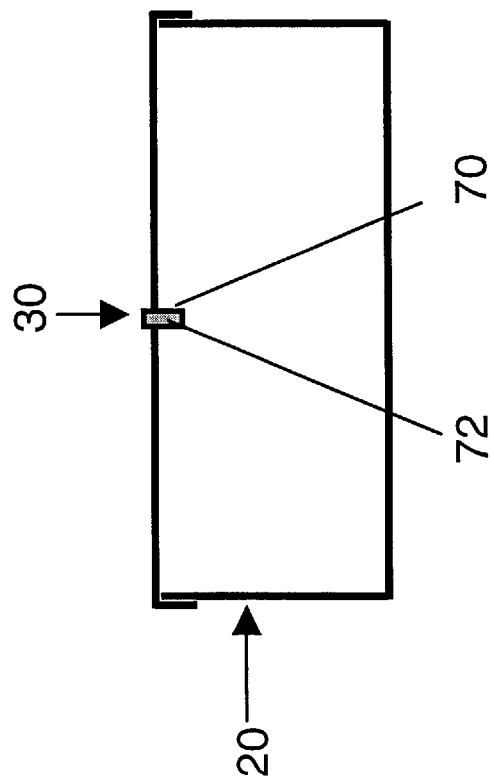

METHOD FOR STERILIZING DEVICES IN A CONTAINER

This application is a continuation-in-part of application Ser. No. 09/105,280, filed Jun. 26, 1998, now U.S. Pat. No. 6,068,817 which is a divisional of application 08/833,375, filed Apr. 4, 1997, now U.S. Pat. No. 5,961,921 which is a continuation-in-part of application Ser. No. 08/628,965, filed Apr. 4, 1996.

BACKGROUND OF THE INVENTION

1. Field of the Invention

This invention relates to an apparatus and a method for sterilizing devices in a container using a source of vaporizable germicide and negative pressure and more particularly, to methods which include the step of contacting the articles or the container containing the articles with a vaporizable germicide prior to exposure to negative pressure or negative pressure combined with plasma.

2. Description of the Related Art

Medical instruments have traditionally been sterilized using either heat, such as is provided by steam, or a chemical, such as formaldehyde or ethylene oxide in the gas or vapor state. Each of these methods has drawbacks. Many medical devices, such as fiberoptic devices, endoscopes, power tools, etc. are sensitive to heat, moisture, or both. Formaldehyde and ethylene oxide are both toxic gases that pose a potential hazard to healthcare workers. Problems with ethylene oxide are particularly severe, because its use requires long aeration times to remove the gas from articles that have been sterilized. This makes the sterilization cycle time undesirably long.

Sterilization using liquid hydrogen peroxide solution has been found to require high concentration of sterilant, extended exposure time and/or elevated temperatures. However, sterilization using hydrogen peroxide vapor has been shown to have some advantages over other chemical sterilization processes (see, e.g., U.S. Pat. Nos. 4,169,123 and 4,169,124). The combination of hydrogen peroxide with a plasma provides certain additional advantages, as disclosed in U.S. Pat. No. 4,643,876, issued Feb. 17, 1987 to Jacobs et al. U.S. Pat. No. 4,756,882, issued Jul. 12, 1988 also to Jacobs et al. discloses the use of hydrogen peroxide vapor, generated from an aqueous solution of hydrogen peroxide, as a precursor of the reactive species generated by a plasma generator. The combination of hydrogen peroxide vapor diffusing into close proximity with the article to be sterilized and plasma acts to sterilize the articles, even within closed packages. Further, these methods of combining hydrogen peroxide vapor with a plasma, while useful in "open" systems, have been found to be inadequate to effect sterilization in articles having diffusion-restricted areas, since the methods are dependent upon diffusion of the sterilant vapor into close proximity with the article before sterilization can be achieved. Thus, these methods have been found to require high concentrations of sterilant, extended exposure time and/or elevated temperatures when used on long, narrow lumens. For example, lumens longer than 27 cm and/or having an internal diameter of less than 0.3 cm have been particularly difficult to sterilize. Thus, no simple, safe, effective method of sterilizing smaller lumens exists in the prior art.

The sterilization of articles containing diffusion-restricted areas, such as long narrow lumens, therefore presents a special challenge. Methods that use hydrogen peroxide vapor that has been generated from an aqueous solution of hydrogen peroxide have certain disadvantages, because:

1. Water has a higher vapor pressure than hydrogen peroxide and will vaporize faster than hydrogen peroxide from an aqueous solution.

2. Water has a lower molecular weight than hydrogen peroxide and will diffuse faster than hydrogen peroxide in the vapor state.

Because of this, when an aqueous solution of hydrogen peroxide is vaporized in the area surrounding the items to be sterilized, the water reaches the items first and in higher concentration. The water vapor therefore becomes a barrier to the penetration of hydrogen peroxide vapor into diffusion restricted areas, such as small crevices and long narrow lumens. One cannot solve the problem by removing water from the aqueous solution and using more concentrated hydrogen peroxide, since, among other reasons, concentrated solutions of hydrogen peroxide greater than 65% by weight can be hazardous due to the oxidizing nature thereof.

U.S. Pat. No. 4,952,370 to Cummings et al. discloses a sterilization process wherein aqueous hydrogen peroxide vapor is first condensed on the article to be sterilized, and then a source of vacuum is applied to the sterilization chamber to evaporate the water and hydrogen peroxide from the article. This method is suitable to sterilize surfaces, however, it is ineffective at rapidly sterilizing diffusion-restricted areas, such as those found in lumened devices, since it too depends on the diffusion of the hydrogen peroxide vapor into the lumen to effect sterilization.

U.S. Pat. No. 4,943,414, entitled "Method for Vapor Sterilization of Articles Having Lumens," and issued to Jacobs et al., discloses a process in which a vessel containing a small amount of a vaporizable liquid sterilant solution is attached to a lumen, and the sterilant vaporizes and flows directly into the lumen of the article as the pressure is reduced during the sterilization cycle. This system has the advantage that the water and hydrogen peroxide vapor are pulled through the lumen by the pressure differential that exists, increasing the sterilization rate for lumens, but it has the disadvantage that the vessel needs to be attached to each lumen to be sterilized. In addition, water is vaporized faster and precedes the hydrogen peroxide vapor into the lumen.

In U.S. Pat. No. 5,492,672, there is disclosed a process for sterilizing narrow lumens. This process uses a multicomponent sterilant vapor and requires successive alternating periods of flow of sterilant vapor and discontinuance of such flow. A complex apparatus is used to accomplish the method. Because flow through of vapor is used, closed end lumens are not readily sterilized in the process.

Thus, there remains a need for a simple and effective method of vapor sterilization of articles having areas where diffusion of these vapors is restricted, such as long, narrow lumens.

SUMMARY OF THE INVENTION

One aspect of the invention relates to a method for sterilizing an article in a diffusion restricted environment under reduced pressure. The method includes placing the article in a container, where the container has at least one communication port and where the container is attachable to and detachable from a vacuum source through the communication port. The method also involves introducing a liquid solution of vaporizable germicide into the container, attaching the container to the vacuum source through the communication port, creating a diffusion restricted environment around the article to be sterilized, where placing, introducing, attaching, and creating can occur in any order, reducing the pressure in the container, generating germicide vapor from the vaporizable germicide, where the germicide vapor diffuses from inside the container through the communication port to outside the container, sterilizing the article in the container. The method also includes detaching the container from the vacuum source, and maintaining the sterility of the article.

Advantageously, the container is also vented through a vapor-permeable and microbe-impermeable filter. In certain embodiments, the pressure in the container is above or below atmospheric pressure when the container is detached from the vacuum source.

In an embodiment, the diffusion restricted environment is created with a diffusion restricted port.

In an embodiment, the diffusion restricted port is at least as diffusion restricted as a port having a length of 1.0 cm, a port having a cross sectional area of 63.62 mm$^2$, or a port having a length/cross sectional area of 0.157 mm$^{-1}$.

Introducing the germicide may involve delivery of the liquid solution containing vaporizable germicide into the container via one or more methods such as injection, static soak, spray or flow-through with liquid or mist, or condensing vapor. The germicide may also be introduced by contacting the article with the liquid solution containing vaporizable germicide.

In an embodiment, the article to be sterilized is a diffusion restricted device. Preferably, the vaporizable germicide contains hydrogen peroxide. Advantageously, the pressure is reduced to below the vapor pressure of the vaporizable germicide during the reducing step.

The communication port may optionally contain a valve. Advantageously, the valve is a hinged valve. Alternatively, the valve is a septum. When the valve is a septum, the method may also include inserting a needlelike device through the septum.

Advantageously, the method may include attaching at least one additional container to the vacuum source. Preferably, the container and the additional containers each contain an article to be sterilized, and the articles can be sterilized independently, simultaneously, in a synchronized manner, in a asynchronized manner, or in a multitasking manner.

In an embodiment, an second container may be nested inside the first container. Advantageously, the second container contains a gas permeable and microbe-impermeable filter. Optionally, the second container is a flexible pouch. Preferably, a liquid solution of vaporizable germicide is in the second container before the pressure is reduced.

Another aspect of the invention concerns a method for sterilizing an article in a container under reduced pressure. The method includes placing the article in the container, where the container has at least one communication port and where the container is attachable and detachable from a vacuum source through the communication port. The method also involves attaching the container to the vacuum source through the communication port, where the placing and the attaching can occur in either order. The method includes reducing the pressure in the container with the vacuum source through the communication port, introducing germicide vapor into the container though the communication port, sterilizing the article. The method also involves detaching the container from the vacuum source and maintaining the sterility of the article.

Advantageously, the method also includes venting the container through a vapor-permeable and microbe-impermeable filter. Preferably, the pressure in the container is above or below atmospheric pressure when the container is detached from the vacuum source. In an embodiment, the germicide vapor contains hydrogen peroxide. Advantageously, the communication port contains a valve.

Preferably, at least one additional container is attached to the vacuum source. Advantageously, the container and the additional container each contain an article to be sterilized, and the articles to be sterilized can be sterilized independently, simultaneously, in a synchronized manner, in a asynchronized manner, or in a multitasking manner. In an embodiment, a second container containing at least one communication port is nested inside the container. Advantageously, the second container contains a gas permeable and microbe-impermeable filter. In an embodiment, the second container is a flexible pouch.

BRIEF DESCRIPTION OF THE DRAWINGS

FIG. 8 is a cross-sectional illustration of one embodiment of a diffusion restricted environment represented by a container with a substantially vertical tube with a filter as a limited diffusion port.

FIG. 9 is a cross-sectional illustration of one embodiment of a diffusion restricted environment represented by a container with a substantially horizontal tube with filter as a limited diffusion port.

DETAILED DESCRIPTION OF THE PREFERRED EMBODIMENT

Figure 1:
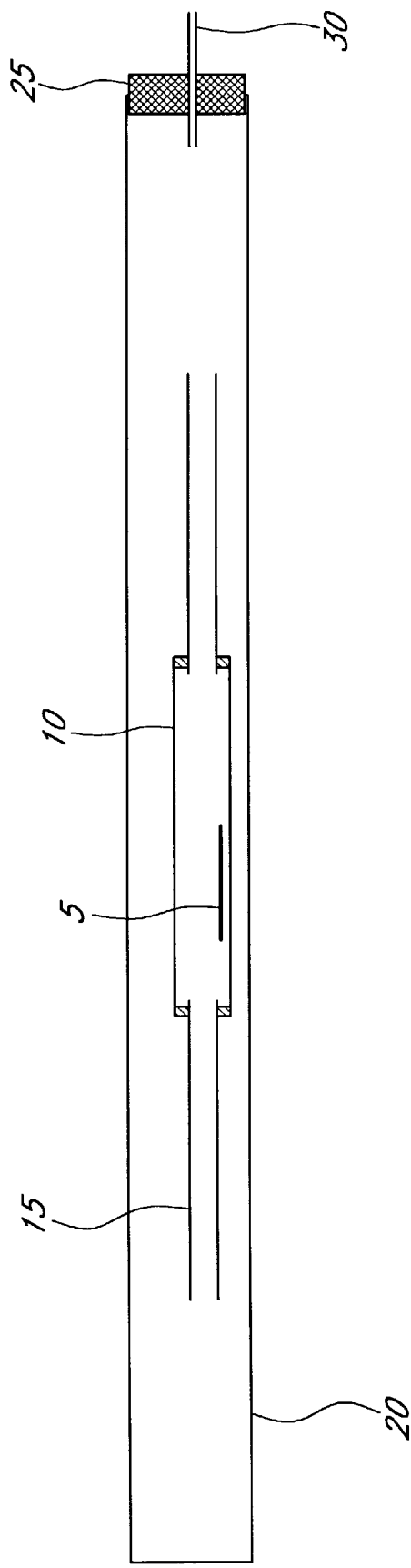
FIG. 1 is a cross-sectional illustration of a lumen containing an inoculated stainless steel blade placed within a glass tube having only a narrow opening to create a diffusion-restricted environment for testing the sterilization method of the present invention.

Sterilizing the inside of lumened devices has always posed a challenge to sterilization systems. Achieving rapid sterilization of lumened devices or other diffusion restricted articles at low temperatures and low concentrations of sterilant represents an even greater challenge. In the present invention, the shortcomings of the prior art sterilization systems are overcome by pretreating or contacting articles to be sterilized with a source of peroxide prior to exposure to a vacuum, or optionally, plasma. Alternatively, a diffusion-restricted environment containing articles to be sterilized can be contacted with a source of peroxide prior to exposure to a vacuum. The source of peroxide comprises a liquid or condensed vapor in the case wherein an article is contacted. In the case wherein a diffusion-restricted environment is contacted, the source of peroxide additionally comprises a solid. The liquid comprises aqueous solutions of hydrogen peroxide or peracetic acid. The solid comprises a urea peroxide complex, or sodium pyrophosphate peroxide complex or like peroxide complex. The vapor comprises hydrogen peroxide or peracetic acid vapor. The preferred method of the present invention utilizes aqueous hydrogen peroxide as the source of peroxide to contact an article to be sterilized. The methods of the present invention provide for the rapid sterilization of lumened and non-lumened articles under conditions that will not damage the articles nor leave toxic residues on the sterile articles.

In the method of the present invention, the source of the peroxide is delivered into direct contact with the article to be sterilized or with the diffusion-restricted environment containing the article to be sterilized. In the case of a lumened device, the source of peroxide may be delivered directly into the lumen. In the case of an article having an area where diffusion of vapor is restricted, the source of peroxide may be delivered to the interior of the diffusion restricted area. For articles which are not diffusion-restricted, the source of peroxide can be introduced anywhere into the diffusion-restricted environment. The source of peroxide is delivered into the lumen or into contact with the article to be sterilized or into contact with the diffusion-restricted environment containing the article to be sterilized through means such as direct delivery or physical placement, a static soaking process, a liquid flow-through process, by aerosol spray or by condensation of a vapor. Physical placement also includes placement of a reservoir containing the source of peroxide. In the preferred method of the present invention, the aqueous solutions of hydrogen peroxide can be relatively dilute, e.g., as low as 1–6% or lower by weight, since sterilization is not achieved through contact with the hydrogen peroxide solution, but rather, is achieved at low temperatures and in short periods of time upon exposure to hydrogen peroxide vapor under vacuum or vacuum combined with plasma. The method of the present invention is particularly effective with articles having inaccessible or hard-to-reach places. Such articles include long, narrow lumens, hinges, mated surface, and other articles having spaces where diffusion of vapors is restricted.

The general operation of one embodiment of a preferred method of the present invention, which is useful for sterilizing the inside of long, narrow lumens, is as follows:

1. The lumen to be sterilized is contacted with a source of peroxide. The source of peroxide can be physically delivered as a small amount directly into the lumen, or by static soaking, liquid flow-through, aerosol spray or condensation of a vapor.

2. The lumen to be sterilized is placed within a chamber, and the chamber is sealed and evacuated. (The source of peroxide can also be delivered to the inside of the article after placing the article in the chamber.)

3. The lumen is exposed to the vacuum for a period of time and at a temperature sufficient to effect sterilization.

4. The sterile lumen is removed from chamber.

In an alternative embodiment of the method of the present invention, a similar method is used to sterilize both the inside and outside of an article. In this alternative embodiment, the article to be sterilized is placed in a diffusion-restricted environment. The diffusion-restricted environment can be a rigid container or flexible pouch having at least one communication port. The communication port can be an exit tube, a hole, or a channel. In this embodiment, the communication port is preferably diffusion-restricted. Alternatively, it is not necessary that the communication port be diffusion-restricted so long as diffusion of sterilant vapor is limited by the article to be sterilized, such as the case wherein sterilant vapor must flow through a limited diffusion area or lumen of an article to be sterilized. This depends upon the configuration of the container. The exit tube may be constructed from a variety of materials, such as glass, metals and plastics and may include a filter. The filter may be sufficient to prevent entry of bacteria from the environment into the container. The source of peroxide is introduced to the inside of the article. The source of peroxide can be introduced either before or after placing the article in the diffusion-restricted environment. The diffusion-restricted environment containing the article to be sterilized is then placed in the chamber, exposed to vacuum and removed as in steps 2 through 4 above.

In an alternative embodiment of the present invention, the device to be sterilized is placed in a diffusion restricted container which can be attached and detached from a source of vacuum. The source of vacuum can be a vacuum chamber or may be a source of vacuum not connected to a vacuum chamber.

The general operation of an alternative embodiment of the method of the present invention, which is also useful for sterilizing the inside of long, narrow diffusion-restricted lumens, is as follows:

1. The article to be sterilized is placed in a diffusion-restricted environment such as a container, said container comprising at least one communication port comprising an exit tube or air and vapor permeable window; and 2. The diffusion-restricted environment is contacted with a source of peroxide, steps 1. and 2. being performed in either order; followed by 3. The diffusion-restricted environment is exposed to negative pressure for a time period sufficient to effect complete sterilization of said article.

The communication port is preferably connected through a connector to the article, so that sterilant vapor may flow through the article and out of the container. In this embodiment, the communication port comprising an exit tube or air and vapor permeable window is also preferably diffusion-restricted. Alternatively, it is not necessary that the communication port, in particular an air and vapor permeable window, be a limited diffusion port so long as diffusion of sterilant vapor is limited by the article to be sterilized, such as the case wherein sterilant vapor must flow through a limited diffusion area or lumen of an article to be sterilized. This depends upon the configuration of the container. The exit tube may be constructed from a variety of materials, such as glass, metals and plastics and may include a filter. The filter may be sufficient to prevent entry of bacteria from the environment into the container. The air and vapor permeable window may be constructed from permeable materials such as Tyvek.

In yet another alternative embodiment of the present invention which pertains to all of the above methods, the article to be sterilized is exposed to a vacuum followed by low temperature plasma for a time sufficient to effect sterilization. When used in the present specification and claims, the term "plasma" is intended to include any portion of the gas or vapor that contains electrons, ions, free radicals, dissociated and/or excited atoms or molecules produced as a result of an applied electric field, including any accompanying radiation that might be produced. The applied field may cover a broad frequency range; however, a radio frequency or microwaves are commonly used.

The sterilization methods of the present invention can also be used with plasmas generated by the method disclosed in the previously mentioned U.S. Pat. No. 4,643,876. Alternatively, the methods of the present invention may be used with plasmas described in U.S. Pat. No. 5,115,166 or 5,087,418, in which the article to be sterilized is located in a chamber that is separated from the plasma source.

The present invention provides several advantages over earlier vapor sterilization systems, such as, (1) the rapid sterilization of lumened devices and diffusion restricted articles can be rapidly achieved at low temperatures; (2) the use of concentrated, potentially hazardous, solutions of anti-microbials is avoided; (3) the need to attach a special vessel to deliver sterilant vapors into long, narrow lumens is eliminated; (4) no toxic residues remain; (5) since the product is dry at the end of the process, sterile storage of these articles can be achieved; (6) closed end lumens can be sterilized; and (7) the process can be repeated as desired without undue effects. The method of the present invention therefore provides for a highly efficient, nonhazardous, and relatively inexpensive method of sterilization.

To determine the efficacy of the preferred sterilization method of the present invention, preliminary tests were first performed to evaluate the effect of dilute hydrogen peroxide solutions on contaminated surfaces in an open, non-diffusion restricted environment. These tests are described below in Example 1.

EXAMPLE 1

To evaluate the sterilization efficacy of dilute hydrogen peroxide solution alone, a biological challenge consisting of $2.5 \times 10^6$ *Bacillus stearothermophilus* spores on a stainless steel scalpel blade was used. Inoculated blades were submerged in 40 ml of hydrogen peroxide solution in a 100 ml beaker. Four different concentrations of hydrogen peroxide solution were used: 3%, 6%, 9% and 120% by weight. The blades were allowed to soak in the peroxide solutions for various time periods. The blades were then removed from the solution and tested for sterility. The results of this testing are listed in Table 1 as a ratio of the number of inoculated blades which remain contaminated after treatment over the number of inoculated blades tested.

TABLE 1

Effect of $H_2O_2$ Concentration and Soak Times on Sporicidal Activity of $H_2O_2$ Solution

| Soak Time | Concentration of $H_2O_2$ Solution | | | |
|---|---|---|---|---|
| | 3% | 6% | 9% | 12% |
| 1 min | 4/4 | 4/4 | 4/4 | 4/4 |
| 5 min | 4/4 | 4/4 | 4/4 | 4/4 |
| 30 min | 4/4 | 4/4 | 4/4 | 4/4 |
| 60 min | 4/4 | 4/4 | 4/4 | 4/4 |
| 90 min | N/D* | 4/4 | 2/4 | 0/4 |
| 120 min | N/D | 4/4 | N/D | N/D |

*N/D = not determined

Complete sterilization was not effected until after the blades had been soaked in 12% hydrogen peroxide solution for at least 90 minutes. Moreover, none of the blades tested were sterilized after 2 hours in 6% hydrogen peroxide solution. It is clear from these data that contact with dilute hydrogen peroxide solution alone is ineffective at providing sterilization, unless extended soak times and concentrated solutions are used.

Testing was next performed to evaluate the effect on the sterilization of long, narrow lumens of a pretreatment step in which the lumens to be sterilized are exposed to hydrogen peroxide solution prior to exposure to a vacuum. The testing evaluated the efficacy of hydrogen peroxide vapor sterilization inside the lumens. The testing is detailed below in Example 2.

EXAMPLE 2

A biological challenge consisting of $1.9 \times 10^6$ *B. stearothermophilus* spores on a stainless steel scalpel blade was used. Some inoculated blades were pre-treated with a solution of aqueous hydrogen peroxide. Other inoculated blades, designated control blades, did not receive pretreatment with hydrogen peroxide. The pretreatment consisted of 5 minutes of static soaking in peroxide solution. The pre-treated blades were blotted dry, and each blade was then placed inside a stainless steel lumen, 3 mm internal diameter (ID)×50 cm length. The lumen had a center piece of 1.3 cm ID and 5 cm length. The pretreated blade was placed inside this center piece, and additional hydrogen peroxide solution was added into the center piece in various amounts. Control blades were handled identically, except that they did not receive pretreatment with hydrogen peroxide solution. The lumens were placed in a vacuum chamber, and the chamber was evacuated to 1 Torr and held there for 15 minutes, during which time the temperature increased from approximately 23° C. to approximately 28° C. Following exposure to the vacuum, the chamber was vented and the blades were removed from the chamber and tested for sterility. The results were as follows:

TABLE 2

Effect of Pretreatment and Hydrogen Peroxide Concentration on Sterilization of the Interior of Lumens

| Additional peroxide added into the center piece | Blades not pre-treated with peroxide | Blades pre-treated in peroxide solution |
|---|---|---|
| (A) With 1% hydrogen peroxide solution and vacuum | | |
| 10 µL | + | + |
| 20 µL | + | + |
| 30 µL | + | + |
| 40 µL | + | + |
| 50 µL | + | + |
| 100 µL | + | − |
| 150 µL | + | − |
| 200 µL | − | − |
| 250 µL | − | − |
| (B) With 3% hydrogen peroxide solution and vacuum | | |
| 10 µL | − | − |
| 20 µL | − | − |
| 30 µL | − | − |
| 40 µL | − | − |
| 50 µL | − | − |
| 100 µL | − | − |
| 150 µL | − | − |
| 200 µL | − | − |
| 250 µL | − | − |

TABLE 2-continued

Effect of Pretreatment and Hydrogen Peroxide Concentration on Sterilization of the Interior of Lumens

| Additional peroxide added into the center piece | Blades not pre-treated with peroxide | Blades pre-treated in peroxide solution |
|---|---|---|
| (C) With 6% hydrogen peroxide solution and vacuum | | |
| 10 µL | – | – |
| 20 µL | – | – |
| 30 µL | – | – |
| 40 µL | – | – |
| 50 µL | – | – |

As seen from these results, sterilization can be effected using relatively dilute solutions of peroxide and exposure to negative pressure. When the vacuum was applied, the peroxide added to the center piece of the lumen was vaporized and contacted the blade, which was sufficient to effect sterilization. It can be seen from these data that the pretreatment increases effectiveness, but that pretreatment is unnecessary as long as the peroxide diffuses from the inside to the outside.

Sterilization inside various lumen sizes after pretreatment with peroxide was compared with sterilization inside the lumens without the pretreatment step. This testing is detailed in Example 3.

EXAMPLE 3

A biological challenge consisting of $1.9 \times 10^6$ *B. stearothermophilus* spores on a stainless steel scalpel blade was used. Test A in Table 3 below consisted of the inoculated blades being pretreated with a solution of 3% aqueous hydrogen peroxide. The pretreatment consisted of 5 minutes of static soaking in the peroxide solution. The pretreated blades were blotted dry, then placed into the center piece of a stainless steel lumen which varied in size, together with 10 µl of 3% hydrogen peroxide solution. The center piece was 1.3 cm ID and 5 cm length. Test B in Table 3 below consisted of identically inoculated control blades which did not receive pretreatment with hydrogen peroxide. Each inoculated control blade was placed directly into the center piece of a stainless steel lumen together with 10 µl of 3% hydrogen peroxide solution. The center piece had dimensions identical to those in Test A. Lumens of various dimensions were used to evaluate the effect on sterilization of lumen internal diameter and length. The lumens were placed in a vacuum chamber, and the chamber was evacuated to 1 Torr for 15 minutes. During this 15 minutes of the sterilization cycle, the temperature increased from approximately 23° C. to approximately 28° C. Following exposure to the vacuum, the chamber was vented and the blades were removed from the chamber and tested for sterility. The results are reported in Table 3, where "LID Ratio" indicates the ratio of length to internal diameter.

TABLE 3

Effect of Pretreatment With Dilute Hydrogen Peroxide in Various Sized Lumens

| SS lumen size | L/D Ratio | Test A | Test B |
|---|---|---|---|
| 1 mm × 50 cm | 500 | – | – |
| 1 mm × 40 cm | 400 | – | – |
| 1 mm × 27 cm | 270 | – | – |
| 1 mm × 15 cm | 150 | – | – |
| 3 mm × 50 cm | 166⅔ | – | – |
| 3 mm × 40 cm | 133⅓ | – | – |
| 3 mm × 27 cm | 90 | – | + |
| 3 mm × 15 cm | 50 | + | + |
| 6 mm × 50 cm | 83⅓ | – | – |
| 6 mm × 40 cm | 66⅔ | – | – |
| 6 mm × 27 cm | 45 | + | + |
| 6 mm × 15 cm | 25 | + | + |

All lumens having a L/D ratio greater than 50 which were tested under the conditions of Test A of Example 3 were sufficiently diffusion-restricted to be sterilized in this system. Thus, it is believed that other lumens having an L/D ratio greater than 50 should also provide a sufficient level of diffusion-restriction for sterilization in accordance with the present invention. This testing shows that, in direct contrast to prior art methods, sterility through diffusion of hydrogen peroxide vapor from inside the article to outside the article is easier to achieve in longer, narrower lumens than in shorter, wider lumens. This is believed to be due to the larger lumens allowing too much of the hydrogen peroxide vapor to diffuse out of the inside of the lumen during the sterilization process. Thus, the vapor does not contact the internal surfaces for a period of time sufficient or at a concentration sufficient to effect sterilization.

As discussed above, prior art methods of hydrogen peroxide vapor sterilization of lumens are generally limited to use on relatively short and wide lumens. In contrast to these prior art methods, the method of the present invention is effective on the interior of long, narrow lumens, including those longer than 27 cm in length and/or having an internal diameter of less than 3 mm.

To determine whether the ability of the sterilant vapor to diffuse within the system is a critical factor in achieving sterility, additional testing was performed to compare diffusion restricted and open, non-diffusion restricted systems. A non-diffusion restricted system is one in which the diffusion of vapors in and around the article is not restricted by narrow openings, long, narrow lumens, or the like. As used herein, "diffusion-restricted" refers to any one or more of the following properties: (1) the ability of an article placed within the sterilization system of the present invention to retain 0.17 mg/L or more hydrogen peroxide solution after one hour at 40° C. and 10 torr; (2) having the same or more diffusion restriction than provided by a single entry/exit port of 9 mm or less in internal diameter and 1 cm or greater in length; (3) having the same or more diffusion restriction than provided by a lumen 27 cm in length and having an internal diameter of 3 mm; (4) having the same or more diffusion restriction than provided by a lumen having a ratio of length to internal diameter greater than 50; (5) the ability of an article placed within the sterilization system of the present invention to retain 17% or more of the hydrogen peroxide solution placed therein after one hour at 40° C. and 10 torr; or (6) being sufficiently diffusion-restricted to completely sterilize a stainless steel blade within a 2.2 cm by 60 cm glass tube having a rubber stopper with a 1 mm by 50 cm stainless steel exit tube therein at a vacuum of 10 torr for one hour at 40° C. in accordance with the present invention. It is acknowledged that characteristics (1) and (5) will vary depending on the initial concentration of hydrogen peroxide placed into the article; however, this can be readily determined by one having ordinary skill in the art.

As discussed in the Background of the Invention, articles having diffusion restricted areas are difficult to sterilize using known methods of hydrogen peroxide vapor sterilization, since these methods are dependent upon the diffusion of peroxide vapors from outside the article to the interior of the article. Testing performed to evaluate the importance of sterilant vapor diffusion is described in Example 4.

EXAMPLE 4

Hydrogen peroxide vapor sterilization was tested in both open and diffusion restricted systems. The open system consisted of stainless steel lumens having internal diameters of 1, 3, and 6 mm, and lengths of 15, 27, 40 and 50 cm. Stainless steel scalpel blades were inoculated with $1.9 \times 10^6$ *B. stearothermophilus* spores, and the blades placed in the center piece of the lumen together with 10 μl of 3% hydrogen peroxide solution. The dimensions of the center piece were 1.3 cm ID, 5 cm length and 6.6 cc volume.

The diffusion restricted system is illustrated in FIG. 1. Identically inoculated scalpel blades 5 were placed within the center pieces 10 of lumens 15 having dimensions identical to those described above. Ten μl of 3% hydrogen peroxide solution was also added to the center piece 10 of the lumen 15. The lumen was then placed within a 2.2 cm×60 cm glass tube 20. The tube 20 was closed at one end, and the open end was plugged with a rubber stopper 25 having a 1 mm×10 cm stainless steel tube 30 inserted through the stopper 25. Thus, gases entering or exiting the glass tube 20 could pass only through this 1 mm×10 cm opening.

The open lumen system and the diffusion restricted system were placed inside a vacuum chamber. The chamber was evacuated to 1 Torr pressure and held there for 15 minutes, during which time the temperature increased from approximately 23° C. to approximately 28° C. The chamber was then vented, and the blades removed from the lumens and tested for sterility. The results are as follows:

TABLE 4

Hydrogen Peroxide Vapor Sterilization in Open and Diffusion Restricted Systems

| System | Peroxide amount | Length | 1 mm ID | 3 mm ID | 6 mm ID |
|---|---|---|---|---|---|
| Open | 10 μL of 3% | 50 cm | – | – | – |
| | | 40 cm | – | – | – |
| | | 27 cm | – | + | + |
| | | 15 cm | – | + | + |
| Diffusion Restricted Environment | 10 μL of 3% | 50 cm | – | – | – |
| | | 40 cm | – | – | – |
| | | 27 cm | – | – | – |
| | | 15 cm | – | – | – |

Under the test conditions of Example 4, sterilization was not achieved in the shorter, wider lumens in the open system without pretreatment with hydrogen peroxide. Pretreatment, and other test conditions, such as higher peroxide concentration or longer treatment time, would likely allow sterilization of the 27 cm×3 mm lumen, which has an LID ratio greater than 50. In the diffusion restricted system, the blades were sterilized in all sizes of lumens, using a 3% hydrogen peroxide solution.

These results indicate that providing a source of hydrogen peroxide within a diffusion restricted environment allows for complete sterilization within the system. It is the restriction of vapor diffusion in the system, not the length or internal diameter of the lumen per se that determines the efficacy of the hydrogen peroxide vapor sterilization. Again, however, these data show that, unlike the prior art methods of hydrogen peroxide vapor sterilization of lumens, the method of the present invention is effective even on non-diffusion-restricted articles when placed into a diffusion-restricted environment.

To further test the idea that restriction of the diffusion of vapor in a system affects the ability to sterilize the system, the following experiment was performed.

EXAMPLE 5

Figure 2:
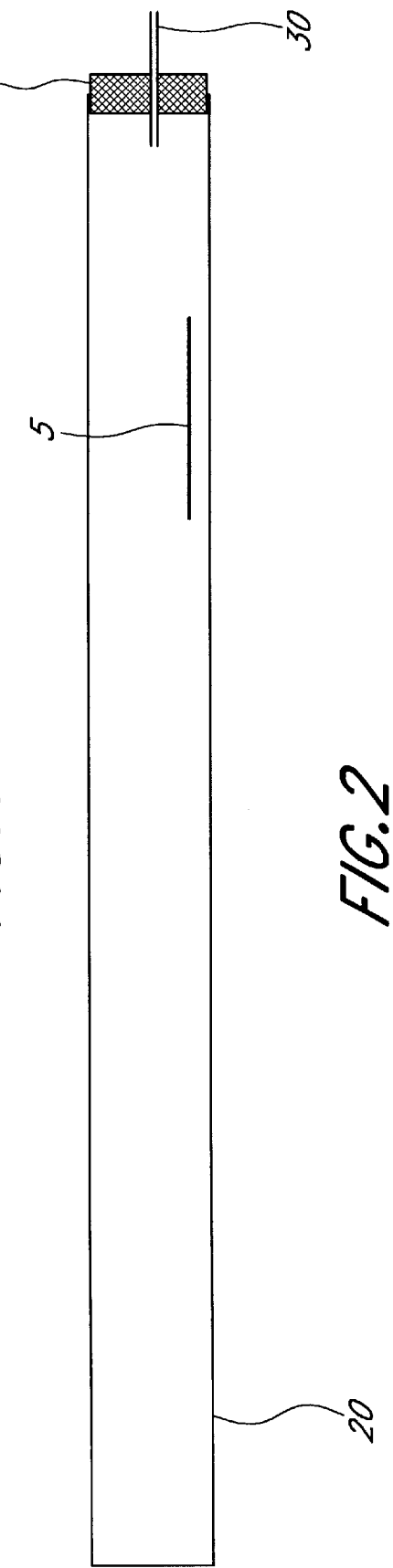
FIG. 2 is a cross-sectional illustration of an inoculated stainless steel blade placed directly within a glass tube having only a narrow opening to create an alternate diffusion-restricted environment for testing the sterilization method of the present invention.

A stainless steel scalpel blade 5 was placed within a 2.2 cm×60 cm glass tube 20 which was closed at one end, as illustrated in FIG. 2. Each blade 5 had been inoculated with $1.9 \times 10^6$ *B. stearothermophilus* spores. For some of the testing, the glass tube 20 was left open at one end, providing an open system. To create a diffusion restricted environment, the open end of the glass tube 20 was sealed with a rubber stopper 25 having a 1 mm×10 cm stainless steel tube 30 through its center. In both the open and diffusion restricted systems, hydrogen peroxide solution at a concentration of either 3% or 6% was added to the glass tube 20 in amounts of 50, 100, 150 or 200 μl, together with the inoculated blade 5. The tube 20 was placed in a vacuum chamber, and the chamber evacuated to 1 Torr for 15 minutes, during which time the temperature increased from approximately 23° C. to approximately 28° C. The diffusion restricted system only was also tested at 1 Torr for 30 minutes, during which time the temperature increased from approximately 23° C. to approximately 33° C. The vacuum chamber was then vented, and the blades 5 removed from the tube 20 and tested for sterility. The results are listed in Table 5 below.

TABLE 5

Hydrogen Peroxide Vapor Sterilization in Open and Diffusion Restricted Systems

| | 50 μL | 100 μL | 150 μL | 200 μL |
|---|---|---|---|---|
| Open System, 15 minutes vacuum at 1 Torr: | | | | |
| 3% peroxide | + | + | + | + |
| 6% peroxide | + | + | + | + |
| Diffusion Restricted System, 15 minutes vacuum at 1 Torr: | | | | |
| 3% peroxide | + | – | – | – |
| 6% peroxide | – | – | – | – |
| Diffusion Restricted System, 30 minutes vacuum at 1 Torr: | | | | |
| 3% peroxide | – | – | – | – |

These results show that the addition of hydrogen peroxide solution, followed by exposure to vacuum, is ineffective for achieving rapid sterilization in an open system. Identical treatment in a diffusion restricted system, by comparison, results in complete sterilization, except at the very weakest concentration of hydrogen peroxide solution in an amount of only 50 μl. Sterilization can be effected, however, by increasing the exposure to the vacuum.

Thus, the method of the present invention, wherein small amounts of hydrogen peroxide solution are delivered to the article to be sterilized prior to exposure to a vacuum, is an effective method of sterilization. The method does not depend on the diffusion of sterilant vapor into the article being sterilized. Rather, the hydrogen peroxide vapor is created by the vacuum within the system. This vapor is prevented from leaving the system too quickly, because the diffusion of the sterilant vapor from the inside of the article to the outside of the article is slowed. In a diffusion restricted environment, the vapor therefore contacts the article to be sterilized for a period of time sufficient to effect complete sterilization. In addition, unlike the prior art methods where the water in the peroxide solution is vaporized first and becomes a barrier to the penetration of the peroxide vapor, the method of the present invention removes any water from the system first, thereby concentrating the hydrogen peroxide vapor remaining in the system. More importantly, in the preferred method of the present invention, the diffusion of vapor is from the inside to outside rather than outside to inside as in the prior art. As a result, diffusion-restriction in the present invention serves to increase the effectiveness of sterilization rather than to decrease the effectiveness, as in the prior art.

To determine the effect of various pressures on a diffusion restricted sterilization system, the following experiment was performed.

EXAMPLE 6

A stainless steel scalpel blade 5 was placed within a 2.2 cm×60 cm glass tube 20 which was closed at one end, as shown in FIG. 2. Each blade 5 had been inoculated with $1.9 \times 10^6$ B. stearothermophilus spores. To create a diffusion restricted environment, the open end of the glass tube 20 was sealed with a rubber stopper 25 having a 1 mm×10 cm stainless steel tube 30 through its center. Hydrogen peroxide solution at a concentration of 3% was added to the glass tube 20 in amounts of 50, 100, 150 or 200 µl, together with the inoculated blade 5. The tube 20 was placed in a vacuum chamber, and subjected to various pressures for 15 minutes, during which time the temperature increased from approximately 23° C. to approximately 28° C. In a further experiment to determine the effect of increased temperature on the system, the tube 20 was first heated to 45° C., then subjected to 50 Torr pressure for 15 minutes. The results were as follows.

TABLE 6

Effect of Temperature and Pressure on a Diffusion Restricted System

| | 50 µL | 100 µL | 150 µL | 200 µL |
|---|---|---|---|---|
| 15 minutes vacuum with 3% hydrogen peroxide solution: | | | | |
| 1 torr pressure | + | – | – | – |
| 5 torr pressure | – | – | – | – |
| 10 torr pressure | – | – | – | – |
| 15 torr pressure | – | – | – | – |
| 20 torr pressure | – | – | – | – |
| 25 torr pressure | – | – | – | – |
| 30 torr pressure | + | + | + | + |
| 35 torr pressure | + | + | + | + |
| 40 torr pressure | + | + | + | + |
| 45 torr pressure | + | + | + | + |
| 50 torr pressure | + | + | + | + |
| 15 minutes vacuum with 3% hydrogen peroxide at 45° C: | | | | |
| 50 torr pressure | – | – | – | – |

These data show that sterilization can be achieved in diffusion restricted environments at pressures up to about 25 Torr at 28° C. At pressures of 30 Torr and higher, sterilization was not achieved; this is believed to be due to the fact that the vapor pressure of hydrogen peroxide at 28° C. is approximately 28 Torr. Thus, at higher pressures, the liquid hydrogen peroxide inside the glass tube was not vaporizing. This was confirmed by the testing done at 50 Torr pressure at 45° C., wherein sterilization was achieved. The vapor pressure of hydrogen peroxide is increased at 45° C., thus, the hydrogen peroxide was vaporized at 50 Torr, effectively sterilizing the blade placed inside the tube.

Accordingly, in order to achieve sterilization using the method of the present invention employing an aqueous solution of hydrogen peroxide, the temperature and pressure within the vacuum chamber should be such that vaporization of the aqueous hydrogen peroxide solution is achieved, i.e. the system should preferably be operated below the vapor pressure of the hydrogen peroxide. The pressure needs to be below the vapor pressure of hydrogen peroxide, such that the hydrogen peroxide solution present in the system is vaporized and diffuses from the interior of the diffusion restricted environment to the outside. Alternatively, the hydrogen peroxide can be vaporized locally where the system remains above the vapor pressure by introducing energy to the site of the peroxide, such as through microwaves, radio waves, or other energy sources.

To further determine the effect of varying the pressure and the temperature in the diffusion restricted system described in Example 6, the following experiments were performed.

EXAMPLE 7

A stainless steel scalpel blade 5 was placed within a 2.2 cm×60 cm glass tube 20 which was closed at one end, as illustrated in FIG. 2. Each blade 5 had been inoculated with $1.9 \times 10^6$ B. stearothermophilus spores. To create a diffusion restricted environment, the open end of the glass tube 20 was sealed with a rubber stopper 25 having a 1 mm×10 cm stainless steel tube 30 through its center. Hydrogen peroxide solution at a concentration of 3% was added to the glass tube 20 in amounts of 50, 100, 150 or 200 µl together with the inoculated blade 5. The tube 20 was placed in a vacuum chamber, and the chamber evacuated to 5 Torr. To vary the pressure within the chamber, the valve to the vacuum pump was closed, such that the pressure within the chamber rose from 5 Torr to 6.15 Torr after 15 minutes, during which time the temperature increased from approximately 23° C. to approximately 28° C. In a second test, the tube 20 was placed in the chamber and the chamber was evacuated to 50 Torr. The temperature of the glass tube 20 was increased to 45° C. after the evacuation of the chamber was complete. The tube 20 was treated for 15 minutes. The results of these tests are reported below.

TABLE 7

Effect of Varying Temperature and Pressure on Diffusion Restricted Sterilization System

| | 50 µL | 100 µL | 150 µL | 200 µL |
|---|---|---|---|---|
| Pressure increased from 5 Torr to 6.15 Torr: | | | | |
| Efficacy Results | – | – | – | – |
| Temperature of the tube increased to 45° C.: | | | | |
| Efficacy Results | – | – | – | – |

These results show that maintaining a constant pressure or temperature is not required in the diffusion restricted environment to effect sterilization. Under the conditions tested, the hydrogen peroxide is vaporized and kept in contact with the device to be sterilized for a time sufficient to effect complete sterilization.

The preferred method of the present invention relies on the delivery of liquid hydrogen peroxide to the article to be sterilized prior to vacuum or plasma treatment. The following testing was performed to determine the effect of the location of the delivery of the hydrogen peroxide within the diffusion restricted environment.

EXAMPLE 8

A stainless steel scalpel blade 5 was inoculated with $1.9 \times 10^6$ B. stearothermophilus spores, and the blade 5 placed in the center piece 10 of a lumen 15 as illustrated in FIG. 1. The dimensions of the center piece 10 were 1.3 cm ID, 5 cm length and 6.6 cc volume, while the lumen itself varied in size, having an ID of 1, 3 or 6 mm, and a length of 15, 27, 40 or 50 cm. The lumen 15 was placed within a 2.2 cm×60 cm glass tube 20. The tube 20 was closed at one end, and the open end was plugged with a rubber stopper 25 having a 1 mm×10 cm stainless steel tube 30 placed through the stopper 25. Thus, gases entering or exiting the glass tube 20 could pass only through this 1 mm×10 cm opening. 10 µl of 3% hydrogen peroxide solution was placed inside the lumen 15, or 100 µl of 3% hydrogen peroxide solution was placed inside the glass tube 20, but outside the stainless steel lumen 15. The glass tube 20 was then placed in a vacuum chamber, which was sealed and evacuated to 1 Torr for 15 minutes, during which time the temperature increased from approximately 23° C. to approximately 28° C. Results of this testing are as follows.

TABLE 8

Effect of Hydrogen Peroxide Solution Placed Outside Inner Lumen

| Peroxide amount | Length | 1 mm ID | 3 mm ID | 6 mm ID |
|---|---|---|---|---|
| 10 µL of 3% in lumen | 50 cm | − | − | − |
| | 40 cm | − | − | − |
| | 27 cm | − | − | − |
| | 15 cm | − | − | − |
| 100 µL of 3% in glass tube | 50 cm | + | + | + |
| | 40 cm | + | + | + |
| | 27 cm | + | + | + |
| | 15 cm | + | + | − |

These data show that, under the test conditions of Example 8, sterilization did not occur within the inner lumen when the hydrogen peroxide solution was placed outside the lumen in a diffusion restricted environment, but that complete sterilization was effected when the hydrogen peroxide solution was placed inside all of the lumens in a diffusion restricted environment. When the hydrogen peroxide vapor must diffuse from outside to inside, the sterilant vapor cannot enter the inner lumen in a diffusion restricted environment unless the lumen is sufficiently large. Thus, when the hydrogen peroxide solution was placed outside the lumen, only the shortest, widest lumens allowed sufficient vapor penetration to allow sterilization inside the lumen. These data confirm that prior art methods which require diffusion of sterilant vapor from outside the article to the interior article cannot achieve sterilization in diffusion restricted environments under these conditions. In contrast, under the same conditions except where the hydrogen peroxide was placed inside the article, allowing hydrogen peroxide to diffuse from inside to outside, complete sterilization occurred with much lower amounts of hydrogen peroxide.

The method of the present invention is therefore useful in environments where diffusion of the sterilant vapor is limited. To evaluate the effect of changes in the amount of diffusion restriction within a diffusion restricted environment, the following testing was performed.

EXAMPLE 9

A stainless steel scalpel blade 5 was inoculated with $1.9 \times 10^6$ B. stearothermophilus spores, and placed in a 2.2 cm×60 cm glass tube 20 as illustrated in FIG. 2. The tube 20 was closed at one end, and the open end was plugged with a rubber stopper 25. Stainless steel tubing 30 of various dimensions was inserted through the stopper 25. Thus, gases entering or exiting the glass tube 20 could pass only through the opening in the tubing 30, which varied from 1 mm to 6 mm in diameter. Three percent hydrogen peroxide solution in volumes ranging from 50 µL to 200 µL was also placed inside the glass tube 20. The glass tube 20 was then placed in a vacuum chamber, which was sealed and evacuated to 5 Torr for 15 minutes, during which time the temperature increased from approximately 23° C. to approximately 28° C. In addition, three lumens were tested at 10 Torr for 15 minutes with 3% hydrogen peroxide. The results of this testing are listed below in Table 9.

TABLE 9

Effects of Tubing Dimension and Vacuum Pressure on Sterilization 15 minutes vacuum at 5 Torr with 3% hydrogen peroxide

| SS tubing | 50 µL | 100 µL | 150 µL | 200 µL |
|---|---|---|---|---|
| 1 mm × 10 cm | − | − | − | − |
| 1 mm × 5 cm | − | − | − | − |
| 1 mm × 2.5 cm | + | − | − | − |
| 3 mm × 10 cm | − | − | − | − |
| 3 mm × 5 cm | − | − | − | − |
| 3 mm × 2.5 cm | + | − | − | − |
| 6 mm × 10 cm | − | − | − | − |
| 6 mm × 5 cm | + | − | − | − |
| 6 mm × 2.5 cm | + | − | − | − |

15 minutes vacuum at 10 Torr with 3% hydrogen peroxide

| SS tubing | 50 µL |
|---|---|
| 1 mm × 2.5 cm | − |
| 3 mm × 2.5 cm | − |
| 6 mm × 2.5 cm | − |

Complete sterilization was achieved in the majority of the environments tested. Sterilization could not be achieved at 5 torr using the shortest length of stainless steel tubing and only 50 µl hydrogen peroxide solution. Greater volumes of hydrogen peroxide must be used in these systems.

These data also confirm that the vacuum pressure affects sterilization efficacy, since the container with the shortest and widest exit tube could provide sterilization at 10 Torr, but not at 5 Torr. At too low pressures (such as pressures below 5 Torr in the conditions tested) however, it appears that the hydrogen peroxide vapor is pulled from the interior of the article being sterilized too quickly, resulting in an insufficient amount of hydrogen peroxide vapor being allowed to contact the interior of the device to effect sterilization. It would appear that although a pressure of 5 torr produces acceptable results, a pressure of approximately 10 Torr is better under the conditions tested.

The method of the present invention has been shown to be effective in diffusion restricted environments of metal and glass. To evaluate whether the method is effective in diffusion restricted environments formed of other materials, the experiments described in Examples 10 and 11 were performed.

EXAMPLE 10

For this testing, a diffusion restricted system was tested. $1.2 \times 10^6$ B. stearothermophilus spores were inoculated onto non-woven polypropylene pieces. As illustrated in FIG. 1, the inoculated pieces 5 were placed inside the center piece 10 of a plastic lumen 15, together with 10 µl of 3% hydrogen peroxide solution. The center piece 10 was made of Teflon™ and had dimensions of 1.3 cm×5 cm. The lumen 15 varied from 1 mm to 6 mm ID, and 15 cm to 50 cm in length. Teflon™ was used for the 1 mm lumen, polyethylene was used for the 3 mm and 6 mm lumen. The lumen 15 was then placed within a 2.2 cm×60 cm glass tube 20. The glass tube 20 was closed on one end, and the open end was sealed with a rubber stopper 25 having a 1 mm×10 cm piece of PTFE tubing 30 through it. The glass tube 20 was placed in the vacuum chamber and treated for 15 minutes at 1 Torr, during which time the temperature increased from approximately 23° C. to approximately 28° C. The results of this testing are set forth below.

TABLE 10A

Sterilization in Diffusion Restricted Systems Using Plastic Lumens

| System | Pressure | Length | 1 mm ID | 3 mm ID | 6 mm ID |
|---|---|---|---|---|---|
| Diffusion Restricted System | 1 torr | 50 cm | – | – | – |
| | | 40 cm | – | – | – |
| | | 27 cm | – | – | – |
| | | 15 cm | – | – | – |

Sterilization in diffusion restricted environments can be effected in both short, wide lumens and long, narrow lumens, regardless of whether metal or plastic is used to form the lumens. Thus, the method of the present invention is an effective sterilization method for diffusion restricted articles, and can be used on a wide variety of such articles, regardless of their composition.

To further confirm this, $2.1 \times 10^6$ B. stearothermophilus spores were inoculated on stainless steel blades, and $1.2 \times 10^6$ B. stearothermophilus spores were inoculated onto non-woven polypropylene pieces. As shown in FIG. 2, the blades 5 or non-woven polypropylene pieces 5 were placed inside a 2.2 cm×60 cm glass tube 20 together with 50 µl of 3% hydrogen peroxide solution. One end of the tube was closed, and the open end was sealed with a rubber stopper 25 having either a 1 mm×10 cm stainless steel tube 30 therein, or a 1 mm×10 cm piece of Teflon™ tubing 30 therein. The glass tube 20 was placed inside a vacuum chamber and treated for 15 minutes at 5 Torr, during which time the temperature increased from approximately 23° C. to approximately 28° C. The results are as follows.

TABLE 10B

Effect of Metal and Plastic on Sterilization in a Diffusion Restricted System

| | SS tubing | Teflon tubing |
|---|---|---|
| Metal blade | – | – |
| Polypropylene | – | – |

Thus, all four combinations of metal and plastic provide for effective hydrogen peroxide vapor sterilization in a diffusion restricted environment. This testing confirms that the method of the present invention is an effective sterilization method for diffusion restricted articles, and can be used on a wide variety of such articles, regardless of the materials used to form them.

Further testing was next performed to evaluate the effect of various temperatures and pressures on the sterilization of a diffusion restricted system. The testing is described below.

EXAMPLE 11

Stainless steel blades were inoculated with $2.1 \times 10^6$ B. stearothermophilus spores. The blades 5 were placed inside a 2.2 cm×60 cm glass tube 20 as illustrated in FIG. 2, along with various amounts of 3% hydrogen peroxide solution. The glass tube 20 was placed in a vacuum chamber and subjected to different pressures and different temperatures for various periods of time. During the sterilization cycles reported in Table 11A, the temperature increased from approximately 23° C. to the temperatures indicated. In the experiments reported in Table 11B, the chamber was heated to approximately 45° C. In an alternative embodiment, rather than heating the chamber, the temperature of the peroxide solution itself can be heated. In the experiments reported in Table 11C, the temperature increased from approximately 23° C. to approximately 28° C. during the 15 minute period of exposure to vacuum.

TABLE 11A

Effect of Time and Volume of Peroxide on Sterilization in a Diffusion Restricted Environment At 5 Torr pressure:

| | 5 min. (approx. 24° C.) | 10 min. (approx. 26° C.) | 15 min. (approx. 28° C.) |
|---|---|---|---|
| 50 µL of 3% peroxide | – | – | – |
| 100 µL of 3% peroxide | – | – | – |
| 150 µL of 3% peroxide | + | – | – |
| 200 µL of 3% peroxide | + | – | – |

TABLE 11B

Effect of Elevated Chamber Temperature and Volume of Peroxide on Sterization in a Diffusion Restricted Environment Chamber at approximately 45° C.:

| | 5 min. |
|---|---|
| 150 µL of 3% peroxide | – |
| 200 µL of 3% peroxide | – |

TABLE 11C

Effect of Pressure and Volume of Peroxide on Sterilization in a Diffusion Restricted Environment With 15 minutes exposure time:

| Approx 28° C. | 1 torr | 5 torr | 10 torr |
|---|---|---|---|
| 20 µL of 3% peroxide | N/D | + | – |
| 50 µL of 3% peroxide | + | – | – |
| 100 µL of 3% peroxide | – | – | – |

Under the test conditions of Example 11, large volumes of hydrogen peroxide solution were ineffective at achieving sterilization when vacuum was applied for only very short periods of time. This is believed to be at least partially because water vaporizes more quickly than hydrogen peroxide. Thus, the water present in the aqueous solution will vaporize first, and more time is needed to vaporize the hydrogen peroxide. This also explains why the larger volumes of hydrogen peroxide solution were effective at achieving sterilization at higher temperatures; the vaporization of the hydrogen peroxide occurs sooner at higher temperatures. Thus, when more water is present in the system, either higher temperatures or more time is required to achieve sterilization.

Again, it would appear from these data that slightly higher pressures, i.e. 10 Torr, achieve more effective sterilization under these conditions. This is believed to be because at higher pressures, more hydrogen peroxide vapor is retained inside the system. At too low a pressure, the hydrogen peroxide vapor is pulled out of the system too quickly.

In order to evaluate a putative minimum concentration of peroxide in the liquid/vacuum system in a diffusion-restricted container, Example 12 was carried out.

EXAMPLE 12

Various concentrations of peroxide were used in a system substantially as described in connection with FIG. 2. In this system, the exit tube 35 was a stainless steel tube having a length of 50 cm and an internal diameter of 1 mm. A stainless steel blade inoculated with $1.9 \times 10^6$ spores of *B. stearothermophilus* was placed within the container which was a 2.2 cm×60 cm glass tube. Various amounts of 3% hydrogen peroxide were introduced into the container. The container was placed in a vacuum chamber of 173 liters, and the pressure reduced to 10 Torr for a period of one hour, during which time the temperature increased from approximately 23° C. to approximately 40° C. Sporicidal activity was evaluated at each concentration of peroxide. In addition, the amount of peroxide remaining in the container after the sterilization process was evaluated by standard titration techniques, whereby the peroxide was reacted with potassium iodide and titrated with sodium thiosulfate. Results are shown in Table 12 where "N/D" indicates not determined.

TABLE 12

| Amount of peroxide in Glass Tube | Sporicidal Activity | Remaining Peroxide |
| --- | --- | --- |
| 0.5 mg/L liquid | + | N/D |
| 0.6 mg/L liquid | + | N/D |
| 0.7 mg/L liquid | + | N/D |
| 0.8 mg/L liquid | + | N/D |
| 0.9 mg/L liquid | + | N/D |
| 1.0 mg/L liquid | − | 0.17 mg/L |

The results reported in Table 12 indicate that 1.0 mg/L of 3% liquid peroxide were required in the system tested to effect sterilization. Further, under the conditions tested, a concentration of 0.17 mg/L of peroxide remaining in the system was sufficient to provide complete sterilization. These data also show that the glass tube used in these experiments provided a sufficient level of diffusion restriction to retain 17% of the hydrogen peroxide placed therein.

We further investigated the effects of length and internal diameter of the exit tube used in a system similar to that of Example 12. This testing is shown in Example 13.

EXAMPLE 13

A system similar to that described above in connection with Example 12, with the exception that 15 minutes of vacuum rather than one hour was used. Thus, the temperature increased only to about 28° C. In this testing, the size of the exit tube 35 was varied, as well as the volume of 3% peroxide solution. The results are reported below in Table 13.

TABLE 13

|  | 50 µl | 100 µl | 150 µl | 200 µl |
| --- | --- | --- | --- | --- |
| Open without tubing | + | + | + | + |
| 6 mm ID × 1 cm length | + | − | − | − |
| 9 mm ID × 1 cm length | + | − | − | − |
| 13 mm ID × 1 cm length | + | + | + | + |

The results show that provided sufficient peroxide is present, the diffusion-restriction provided by a single entry/exit port of 9 mm or less in internal diameter, or 1 cm or greater in length is sufficient to effect sterilization.

To further evaluate the effect on sterilization efficacy of changes in the amount of restriction of vapor diffusion in the system, the following testing was performed.

EXAMPLE 14

Figure 3:
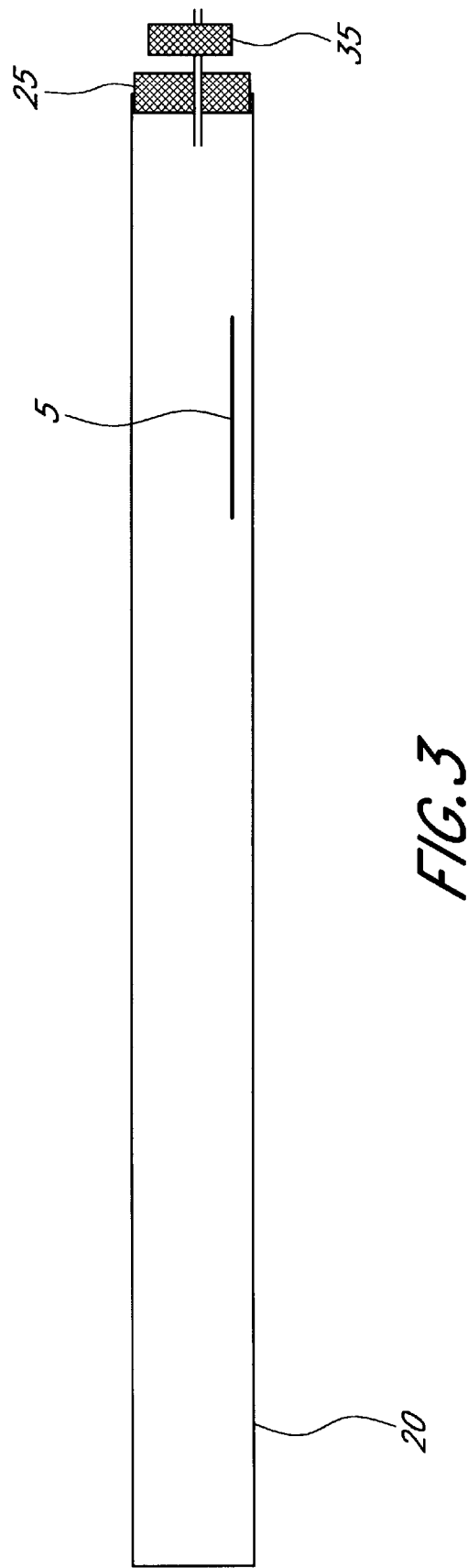
FIG. 3 is a cross-sectional illustration of an inoculated stainless steel blade placed directly within a glass tube having a filter placed at its narrow opening to create an alternate diffusion-restricted environment for testing the sterilization method of the present invention.

A stainless steel blade was inoculated with $2.1 \times 10^6$ *B. stearothermophilus* spores. The blade 5 was placed inside a 2.2 cm×60 cm glass tube 20 as shown in FIG. 3, together with various amounts of 3% hydrogen peroxide solution. One end of the tube was closed, and the open end was sealed with a rubber stopper 25 having a syringe filter 35 inserted therein. The glass tube 20 was placed inside a vacuum chamber and treated for 15 minutes at 5 Torr, during which time the temperature increased from approximately 23° C. to approximately 28° C. As a control, identically inoculated blades were placed inside 2.2 cm×60 cm glass tubes. The open end of the tubes was left open, no stopper or syringe filter was used. Thus, the diffusion of vapor from the interior of the tube was not restricted.

Various syringe filters having various pore sizes were tested, including MFS PTFE 25 mm syringe filters with a 0.2 µm membrane filter and a 0.5 µm membrane filter; a Nalgene PTFE 50 mm syringe filter with a 0.2 µm membrane filter and a 0.45 µm membrane filter; a Whatman Anotop™ 10 Plus sterile syringe filter with a 0.02 µm membrane filter and a 0.1 µm membrane filter; and finally, a Gelman Acrodisc™ CR PTFE syringe filter with a 0.2 µm, 0.45 µm, and a 1.0 µm membrane. The results are as follows.

TABLE 14

Sporicidal Activity of $H_2O_2$ Solution with Vacuum in a Container Having a Syringe Filter
15 minutes vacuum and 3% hydrogen peroxide:
(a) Without syringe filter and stopper:

|  | 50 µl | 100 µL | 150 µL | 200 µL |
| --- | --- | --- | --- | --- |
| 5 Torr | + | + | + | + |
| 10 Torr | + | + | + | + |

(b) With MFS ™ PTFE 25 mm syringe filter:
(1) 0.2 µm membrane filter

|  | 50 µL | 100 µL | 150 µL | 200 µL |
| --- | --- | --- | --- | --- |
| 5 Torr | + | − | − | − |
| 10 Torr | − | − | − | − |

TABLE 14-continued (2) 0.5 μm membrane filter

| | 50 μL | 100 μL | 150 μL | 200 μL |
|---|---|---|---|---|
| 5 Torr | + | − | − | − |
| 10 Torr | − | − | − | − |

(3) With 2 MFS ™ filters together at 5 Torr pressure

| | 50 μL |
|---|---|
| Two 0.2 μm filters | − |
| Two 0.5 μm filters | − |

(c) With Nalgene ™ PTFE 50 mm syringe filter:
(1) 0.2 μm membrane filter

| | 50 μL | 100 μL | 150 μL | 200 μL |
|---|---|---|---|---|
| 5 Torr | − | − | − | − |
| 10 Torr | − | − | − | − |

(2) 0.45 μm membrane filter

| | 50 μL | 100 μL | 150 μL | 200 μL |
|---|---|---|---|---|
| 5 Torr | − | − | − | − |
| 10 Torr | − | − | − | − |

(d) With Whatman Anotop ™ 10 Plus syringe filter:
(1) 0.02 um membrane filter

| | 50 μL | 100 μL |
|---|---|---|
| 5 Torr | − | − |
| 10 Torr | − | − |

(2) 0.1 μm membrane filter

| | 50 μL | 100 μL |
|---|---|---|
| 5 Torr | − | − |
| 10 Torr | − | − |

(e) With Gelman Acrodisc ™ CR PTFE syringe filter:
(1) 0.2 μm membrane filter

| | 50 μL | 100 μL |
|---|---|---|
| 5 Torr | + | − |
| 10 Torr | − | − |

(2) 0.45 μm membrane filter

| | 50 μL | 100 μL |
|---|---|---|
| 5 Torr | + | − |
| 10 Torr | − | − |

(3) 1.0 μm membrane filter

| | 50 μL | 100 μL |
|---|---|---|
| 5 Torr | + | − |
| 10 Torr | − | − |

As is apparent from these results, certain brands of filters do not create a sufficiently diffusion restricted environment at 5 Torr pressure when only 50 μL of hydrogen peroxide solution is placed in the system. Other brands of filters did provide sufficient diffusion restriction; these brands of filters had either longer lumens or smaller filter pore size. Using larger volumes of peroxide solution, 10 Torr pressure, or serial filters enhances the efficacy of the sterilization system. This is important, as filters, including ones made of Tyvek™, are often used in packaging of sterile articles to prevent recontamination with bacteria. These filters generally have a pore size of 1 μm or less, or in the case of Tyvek™, create a tortuous path which bacteria cannot cross. In the present invention, filters can be used in combination with other packaging means to create a diffusion restricted environment to effect sterilization, and the sterile article can remain inside the packaging during storage prior to use; the filter will prevent recontamination of the sterile article.

Figure 4:
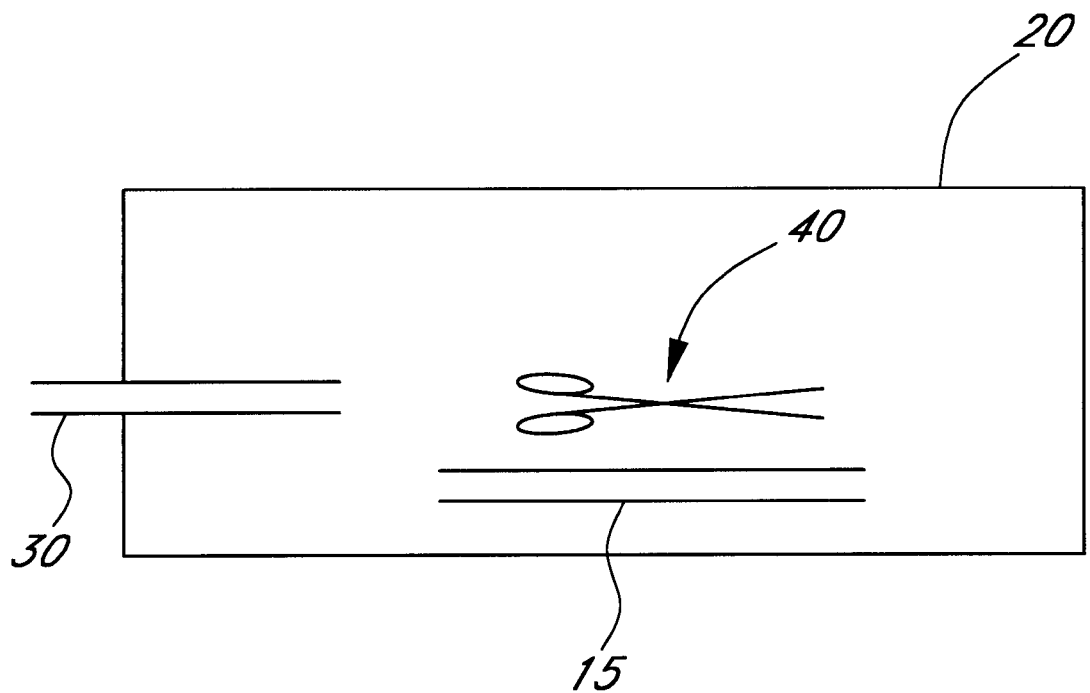
FIG. 4 is a cross-sectional illustration of one embodiment of a diffusion restricted environment represented by a container having a limited diffusion port (communication port consisting of tubing).

FIG. 4 is a cross-sectional illustration of one embodiment of a diffusion restricted environment represented by a container having a limited diffusion port or communication port consisting of tubing. This communication port 30 may have an air permeable microorganism barrier such as a filter in order to maintain a sterility of the devices 15 and 40 in the container 20 after the container 20 is removed from the vacuum source. The non-lumen device 40 and the exterior of the lumen device 15 can be sterilized with the peroxide vapor generated from the source of peroxide within the container 20. In one method of efficiently sterilizing the interior of the lumen device 15, the peroxide vapor needs to be generated within the lumen device 15. Therefore, the lumen device 15 needs to be pre-treated with liquid peroxide.

Figure 5A:
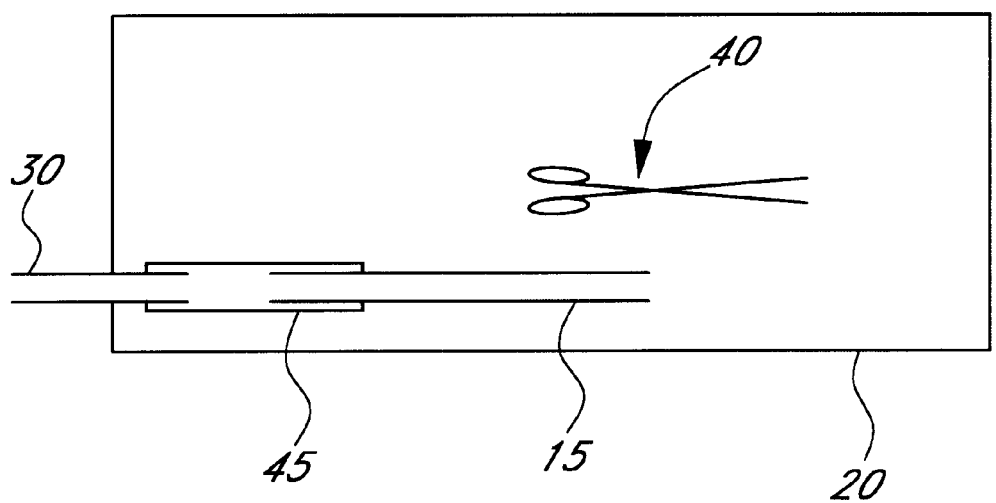
FIG. 5A is a cross-sectional illustration of one embodiment of a diffusion restricted environment represented by a container having a limited diffusion port (communication port consisting of tubing or the lumen device) and a tubing connector to connect a lumen device to the communication port of the container.
Figure 5B:
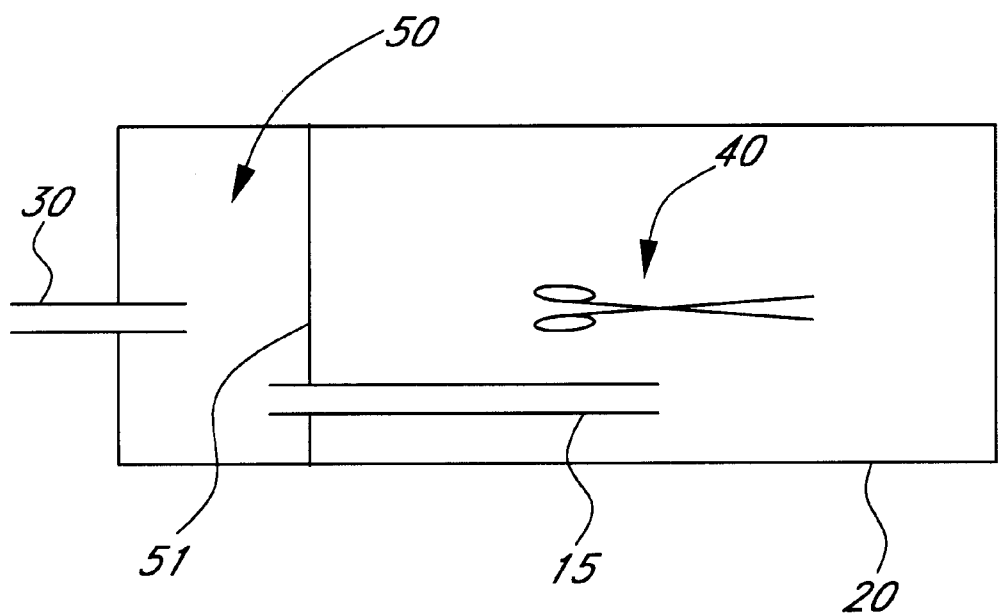
FIG. 5B is a cross-sectional illustration of one embodiment of a diffusion restricted environment represented by a container having a limited diffusion port (communication port consisting of tubing or the lumen device) and an enclosure connector to connect a lumen device to the communication port of the container.
Figure 6:
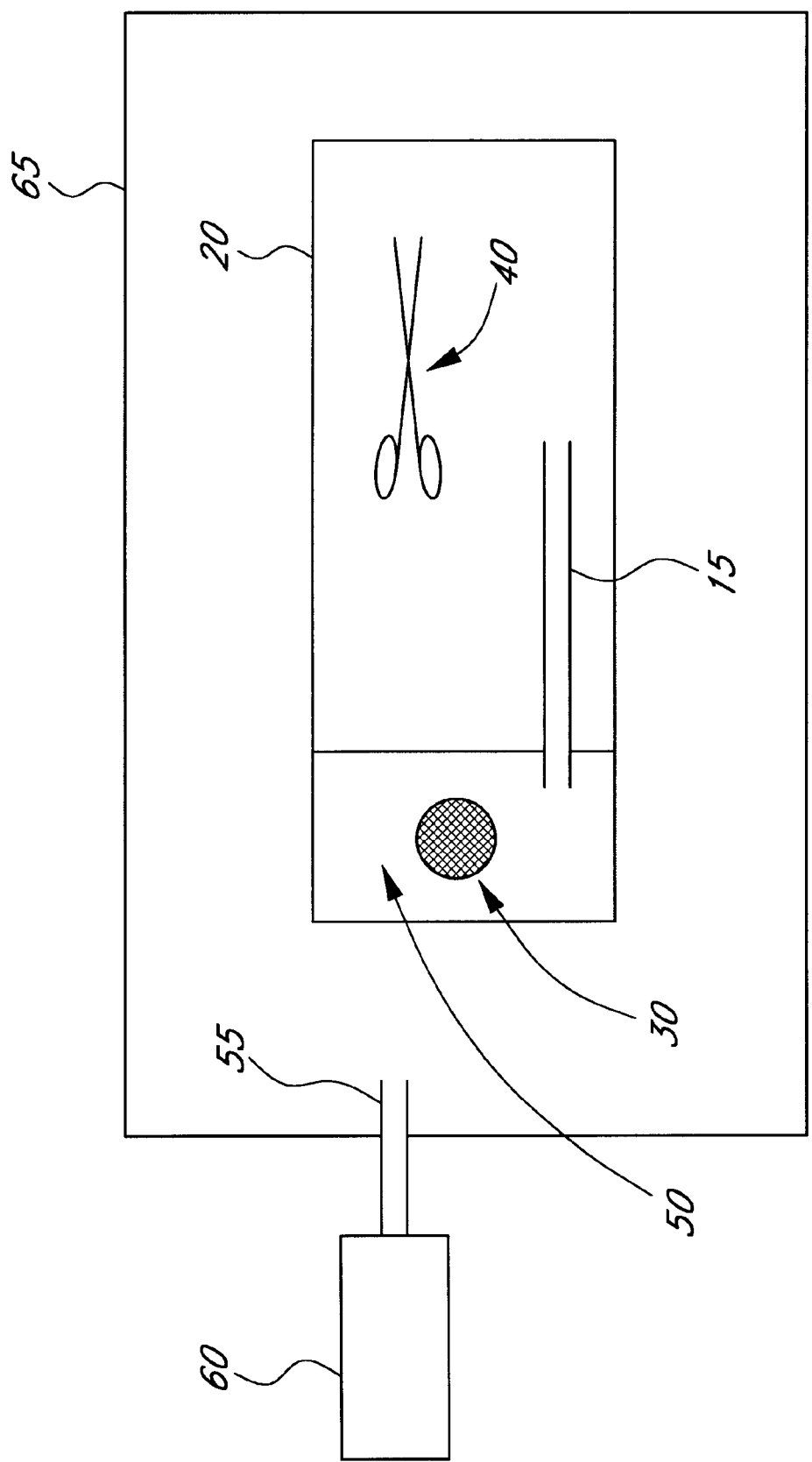
FIG. 6 is a cross-sectional illustration of one embodiment of a diffusion restricted environment represented by a container having a limited diffusion port and an enclosure connector to connect a lumen device to the window.

FIGS. 5–6 illustrate other embodiments of the present invention employing other packaging means to create a diffusion-restricted environment to effect sterilization. Another approach can be used to sterilize the interior of lumen device 15 without pre-treating the interior of lumen device 15 with the source of peroxide. In order to flow the peroxide vapor generated inside container 20 through the interior of lumen device 15, a connector can be used to connect the lumen device 15 to the communication port 30 of the container 20. FIGS. 5A and 5B illustrate this approach. FIG. 5A is a cross-sectional illustration of one embodiment of a diffusion restricted environment represented by a container 20 having a limited diffusion port or communication port 30, consisting of tubing, and a tubing connector 45 to connect a lumen device 15 to the communication port 30 of the container 20. FIG. 5B is a cross-sectional illustration of one embodiment of a diffusion restricted environment represented by a container 20 having a limited diffusion port (communication port 30 consisting of tubing) and an enclosure connector 50 to connect a lumen device 15 to the communication port 30 of the container 20. The enclosure connector 50 has an interface 51 between the container 20 and the enclosure connector 50. This interface 51 can be constructed in several different ways so as to allow a portion of the lumen device 15 to be inserted into the connector enclosure 50, while maintaining an air and vapor pressure seal between parts 15 and 50. One way to achieve this is with a camera shutter approach employing an iris diaphragm, such as a precision iris diaphragm from Edmund Scientific. An optional spring can be used to insure the closure of the shutter. Another way to achieve an acceptable interface is to employ two plates, wherein the area between the two plates has a compressible material, such as a rubber material. The lumen device 15 can be placed between the two plates and the two plates moved together to form a gas and vapor impermeable seal around the lumen device 15. Optionally, a porous material like a sponge or air permeable material may be utilized for the compressible material. In this case, some vapor sterilant can diffuse between the compressible material and the lumen device. However, most of the sterilant vapor is forced to diffuse through the lumen device. Yet another way to achieve an acceptable interface is to employ a hole or horizontal opening for one or more lumen devices 15, said hole or opening being a gas or liquid inflatable port. Thus, the connector can be a tubing adapter 45 which can be attached to the lumen device 15 or an enclosure 50 which contains a portion of the lumen device 15. Since one of the openings of the lumen device 15 is connected to the communication port 30 with the connector 45 or 50, the vaporized peroxide has to be evacuated through the lumen device 15. Tubing connector 45 can be constructed of any materials such as silicone, Teflon, etc. which meet the thermal, pressure, gas and vapor compatibility requirements of the system. These same considerations apply to materials utilized for other parts illustrated herein. Note that the limited diffusion port can be created by either the communication port 30 or the lumen device 15.

FIG. 6 illustrates another possible arrangement. FIG. 6 is a cross-sectional illustration of one embodiment of a diffusion restricted environment represented by a container 20 having a communication port 30 consisting of a window with an air permeable barrier and an enclosure connector 50 to connect a lumen device 15 to the window 30. In this embodiment, the lumen device 15 is connected to the connector 50 and is used as the device to create the diffusion restricted area in the container 20. Therefore, the communication port 30 in FIGS. 4, 5A and 5B can be replaced with an air permeable window 30 if desired. This porous window 30 allows the diffusion of air and vapor, but prevents microorganisms from outside from contaminating the sterilized instruments 15 or 40 in the container or pouch 20. Under the reduced pressure environment, the peroxide vapor is first generated in the container or pouch 20 and then diffuses through the lumen device 15 into the connector 50. The entire connector 50 can be made of air permeable material. FIG. 6 additionally illustrates how the reduced pressure is to be achieved. This is achieved via a port 55 in the vacuum chamber 65, said port being connected to a vacuum pump 60 to produce the reduced pressure environment. In order to test whether other sterilants can also be used to effect sterilization in diffusion restricted environments, the following testing was performed.

EXAMPLE 15

A stainless steel blade was inoculated with $1.\times10^6$ $B.$ $stearothermophilus$ spores. The blade 5 was placed inside a 2.2 cm×60 cm glass tube 20 as shown in FIG. 2, along with various amounts of 4.74% peracetic acid solution (Solvay Interox Ltd., Warrington, England). The glass tube 20 was placed in a vacuum chamber and subjected to 5 Torr pressure for 15 minutes, during which time the temperature increased from approximately 23° C. to approximately 28° C. The results of this testing is shown below.

TABLE 15

Sterilization With Peracetic Acid in a Diffusion Restricted System

| | 50 μL | 100 μL | 150 μL | 200 μL |
|---|---|---|---|---|
| Efficacy Results | – | – | – | – |

These results show that peracetic acid, in which hydrogen peroxide coexists, can also be used in the sterilization method of the present invention.

It was discovered that by delivering small amounts of hydrogen peroxide solution to an article to be sterilized prior to exposure to vacuum, sterilization could be effected at lower temperatures and in short periods of time. The following testing was performed to evaluate different methods of delivering hydrogen peroxide solution to the article to be sterilized. Further, the efficacy of vacuum treatment and plasma treatment following pretreatment with aqueous hydrogen peroxide were compared. The testing is described in Example 16 below.

EXAMPLE 16

In a first series of tests, stainless steel blades were inoculated with $2.5\times10^6$ $B.$ $stearothermophilus$ spores. The blades were placed in the expanded center piece of a 3 mm×50 cm stainless steel lumen. The lumen was placed in a 1000 ml beaker containing 800 ml of hydrogen peroxide solution. The lumen was soaked for 5 minutes in 3% hydrogen peroxide solution. The number of surviving organisms following this initial soak was determined. The lumens were removed from the hydrogen peroxide solution and the outside blotted dry with paper towels. The inside of the lumens were dried by placing one end of the lumen into a flask and blowing with a three second burst of compressed air. The lumens were shaken, and the blowing and shaking repeated until no more solution was blown out. Subsequently, the lumen was placed in a sterilization chamber and exposed to either a vacuum of 0.5 Torr for 15 minutes, or plasma for 15 minutes at 0.5 Torr. After 15 minutes of vacuum, the temperature increased from approximately 23° C. to approximately 28° C. The results are set forth below in Table 16A.

TABLE 16A

Effect of $H_2O_2$ Solution Soak on Sporicidal Activity in Stainless Steel Lumens Prior to Either a Plasma or a Vacuum Treatment

| Conc. $H_2O_2$ (%) Soak Time 5 min | Number of Surviving Organisms After Soaking Alone | Sterility Test Results | | |
|---|---|---|---|---|
| | | Soak Alone | Soak + Vacuum | Soak + Plasma |
| 3.0 | $8.2 \times 10^5$ | 4/4 | 0/4 | 0/4 |

A five minute soak in 3% hydrogen peroxide solution was an effective means for delivering the hydrogen peroxide into the lumen prior to vacuum or plasma treatment. As noted before, treatment with hydrogen peroxide solution only is ineffective to achieve sterilization using dilute solutions and short soak times. Delivery of hydrogen peroxide solution via static soaking is at least as effective a way to deliver the hydrogen peroxide as depositing small volumes directly into the lumen of the device.

Flow-through delivery of hydrogen peroxide was tested next. Here, stainless steel blades were inoculated with $2.5-10^6$ $B.$ $stearothermophilus$ spores. The blades were placed in the expanded center piece of a 3 mm×50 cm stainless steel lumen. Hydrogen peroxide solution at 3% concentration was delivered to the lumen at a flow rate of 0.1 μL/min, using a peristaltic pump. The lumen was dried as described above. Following pretreatment with hydrogen peroxide solution, the lumen was then placed in a sterilization chamber and exposed to either a vacuum of 0.5 Torr for 15 minutes, or plasma for 15 minutes at 0.5 Torr. The results are set forth below in Table 16B.

TABLE 16B

Effects of Flow-Through Delivery of $H_2O_2$ Solution on Sporicidal Activity Prior to Either a Vacuum or a Plasma Treatment in Stainless Steel Lumens

| Conc. $H_2O_2$ | Number of Surviving | Sterility Test Results | |
|---|---|---|---|
| (%) 5 min flow | Organisms after Flow Alone | Flow + Vacuum | Flow + Plasma |
| 3 | $6.2 \times 10^5$ | 0/4 | 0/4 |

Delivery of the hydrogen peroxide solution via constant flow is also an effective way to deliver hydrogen peroxide to the system.

Finally, the effect of delivery of hydrogen peroxide by aerosol spray was tested. Stainless steel blades were inoculated with $2.5 \times 10^6$ B. stearothermophilus spores. The inoculated blades were placed in the expanded center piece of a 3 mm×50 cm stainless steel lumen. Three percent hydrogen peroxide solution was delivered to the lumen via a 3 second aerosol spray. Aerosol spray rate was determined to be 0.04 $\mu$L/min. After a 5 minute wait following pretreatment with hydrogen peroxide, the lumen was dried as described above and the lumen was then placed in a sterilization chamber and exposed to either a vacuum of 0.5 Torr for 15 minutes, or plasma for 15 minutes at 0.5 Torr. The results are set forth below in Table 16C.

TABLE 16C

Effects of Aerosol Delivery of $H_2O_2$ Solution on Sporicidal Activity Prior to Either a Vacuum or a Plasma Treatment in Metal Lumens

| Conc. $H_2O_2$ (%) | Number of Surviving Organisms after Aerosol Alone | Sterility Test Results | |
|---|---|---|---|
| | | Aerosol + Vacuum | Aerosol + Plasma |
| 3 | $7.4 \times 10^5$ | 0/4 | 0/4 |

Flow-through of hydrogen peroxide as either a liquid solution or aerosol can also be achieved by introducing increased pressure at the delivery end or decreased pressure at the exit end of the device to be treated.

It is evident from the data in Tables 16A–16C that all three methods of delivering hydrogen peroxide solution to the article to be sterilized provided for effective sterilization. Thus, it appears that a number of different methods of delivery can be used, as long as the hydrogen peroxide solution is present in the system prior to exposure to vacuum or plasma.

Finally, the efficacy of pretreatment with hydrogen peroxide prior to a sterilization cycle which combines exposure to hydrogen peroxide vapor, vacuum, and plasma was evaluated. The testing was as follows.

EXAMPLE 17

Stainless steel blades were inoculated with $2.5 \times 10^6$ B. stearothermophilus spores. The blades were soaked in 3% hydrogen peroxide solution for either 1 or 5 minutes. The blades were then placed in the expanded center piece of a 3 mm×50 cm stainless steel lumen. The lumen was then placed in a sterilization chamber which was evacuated to approximately 0.5 Torr. The sterilization cycle consisted of 15 minutes of hydrogen peroxide vapor diffusion with a minimum of 6 mg/L hydrogen peroxide, followed by 15 minutes of plasma at 400 watts. Following the plasma treatment, the chamber was vented and the blades tested for sterility. The results are shown below.

TABLE 17

Effects of $H_2O_2$ Solution Soak on Sporicidal Activity in Stainless Steel Lumens Prior to a Hydrogen Peroxide Vapor and Plasma Cycle

| Conc $H_2O_2$ | Soak Time | Sterility Test Results | |
|---|---|---|---|
| | | Soak Alone | Soak + Cycle |
| 3% | 1 min | 4/4 | 0/4 |
| | 5 min | 4/4 | 0/4 |

Processing the lumens in a hydrogen peroxide vapor and plasma cycle alone left an average of 30 surviving organisms per blade. Pretreating the blades by soaking in 3% hydrogen peroxide solution for 5 minutes alone left an average of $8.2 \times 10^5$ surviving organisms per blade. Thus, under these particular test conditions, a combination of hydrogen peroxide vapor exposure and plasma exposure, which has been found to be effective for many articles, was ineffective in a diffusion restricted environment. However, by pretreating the article to be sterilized with dilute hydrogen peroxide solution prior to exposure to hydrogen peroxide vapor and plasma, complete sterilization can be achieved.

Alternative Forms of Diffusion-Restricted Container

The Figures below illustrate various alternative embodiments of diffusion-restricted containers which can be used in embodiments of the method of the invention. In an embodiment of the method of the invention, an article to be sterilized is placed into a diffusion-restricted container, a liquid solution comprising a vaporizable germicide is placed inside the diffusion restricted container or onto the article which is to be sterilized, and the diffusion restricted container with the enclosed article is exposed to vacuum to vaporize the germicide, sterilizing the article. Optionally, the article may be exposed to plasma.

In another embodiment of the method of the invention, the article to be sterilized comprises a diffusion-restricted area such as a lumen, hinge, or mated surface. In the alternative embodiment of the method of the invention, a liquid solution comprising a vaporizable germicide is placed inside the diffusion-restricted area before the diffusion restricted container with the enclosed article is exposed to vacuum to vaporize the germicide. By placing the germicide into the diffusion-restricted area of the article, both the interior and the exterior of the diffusion-restricted article can be sterilized.

Although a wide range of vaporizable germicides may be utilized in the method, hydrogen peroxide, and peracetic acid are exemplary vaporizable germicides for use in the methods of the present invention. It is to be understood that, although the vaporizable germicide may be described as "peroxide", the methods and apparatus are not limited to hydrogen peroxide and peracetic acid but are applicable to a wide range of vaporizable germicides including, but not limited to, hydrogen peroxide, peracetic acid, or glutaraldehyde.

Further, although the containers are described as diffusion-restricted containers, the diffusion restriction need not necessarily occur in the container. The diffusion restriction may occur elsewhere in the system between the container and the source of vacuum.

Although the communication ports 30 which have been described thus far have been either exit tubes or windows, and the shapes of the communication ports 30 in the Figures have been round, the communication ports 30 or entry/exit ports are not limited to exit tubes, windows, or a circular shape. Other embodiments of communication ports 30 or entry/exit ports are given in the Figures below.

FIGS. 7A–7D show various shapes of communication ports 30 or entry/exit ports which are suitable for use in embodiments of the invention. Any of the embodiments of the communication ports 30 can have these shapes. Further, the shapes shown in FIGS. 7A–7D are illustrative only. Other shapes are also suitable for embodiments of communication ports 30 for use in the embodiments of the invention.

Figure 7B:
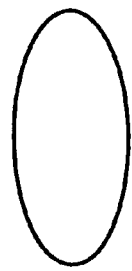
FIG. 7B is a schematic diagram of an oval diffusion restricted port.
Figure 7D:
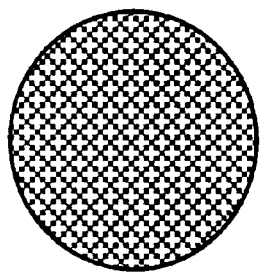
FIG. 7D is a schematic diagram of a round diffusion restricted port covered and/or filled with a filter.
Figure 7A:
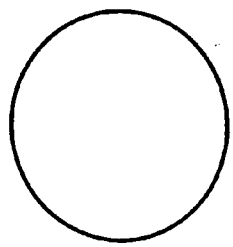
FIG. 7A is a schematic diagram of a round diffusion restricted port.

FIG. 7A shows a communication port 30 having a circular shape. FIG. 7B shows a communication port 30 having an oval shape. The communication port 30 of FIG. 7C has a rectangular shape with rounded corners. The communication port 30 of FIG. 7D is round but is covered and/or filled with a filter 72.

Figure 7C:
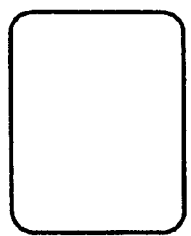
FIG. 7C is a schematic diagram of a rectangular diffusion restricted port.

The shapes of communication ports 30 of entry/exit ports shown in FIGS. 7A–7D are suitable shapes for any of the embodiments of entry/exit ports. The shapes are suitable for both the embodiments of communication port 30 which have been described thus far such as exit tubes or windows and for the embodiments of entry/exit ports described below. For example, the exit tubes in the previous Examples were round exit tubes. Exit tubes with cross sections having an oval shape as shown in FIG. 7B are equally suitable to exit tubes having the round shape of FIG. 7A. Similarly, exit tubes having a rectangular cross section as in FIG. 7C are suitable. The exit tube having a round cross section may be covered and/or filled with a filter 72 as shown in FIG. 7D. Similarly, entry/exit ports which are windows may have the shapes shown in FIGS. 7A–7D. It is to be understood that the shapes of the alternative entry/exit ports or communication ports 30 described below may also have the shapes shown in FIGS. 7A–7D or other suitable shapes.

The criteria for determining whether the various embodiments of entry/exit port with various shapes cause diffusion restriction are similar to the criteria for determining whether exit tubes create diffusion restriction. An exit tube at least 1.0 cm in length can cause diffusion restriction. Similarly, an entry/exit port at least 1.0 cm in length can cause diffusion restriction, regardless of its shape. An exit tube having an internal diameter of 9 mm or less can cause diffusion restriction in a container 20. An exit tube having an internal diameter of 9 mm or less has a cross sectional area of 63.62 mm² or less. Entry/exit ports having alternative shapes such as shown in FIGS. 7A–7D can also cause diffusion restriction, where the entry/exit ports have cross sectional areas of 63.62 mm² or less, regardless of their shape. Where the entry/exit port is filled with, for example, a filter 72, as shown in FIG. 7D, the cross sectional area of the entry/exit port is reduced by the area filled with the solid portions of the filter 72. If the solid portion of the filter 72 covers 10% of the cross sectional area of the entry/exit port, for example, the cross sectional area of the entry/exit port will be reduced 10% by the filter 72. An entry/exit port which is filled with the filter 72 which covers 10% of the cross sectional area will have to have a cross sectional area of 70.69 mm² (63.62 mm²/0.9) or less in order to cause diffusion restriction. Thus, although the scope of entry/exit ports which can cause diffusion restriction is broad, there are criteria for determining whether entry/exit ports of different shapes, for example as shown in FIGS. 7A–7D, can cause diffusion restriction. A diffusion restricted environment can be created with a diffusion restricted port having a length of at least 1.0 cm or a cross-sectional area of 63.62 mm² or less. Alternatively, the diffusion restriction in the container may result from an entry/exit port with a length/cross sectional area of at least 10 mm/66.62 mm$_2$ or 0.157 mm$^{-1}$.

In general, it is a preferred embodiment to have a filter 72 over and/or in the entry/exit port, where the filter 72 is permeable to gases but impermeable to microorganisms. If the entry/exit port is covered and/or filled with a filter 72, the container 20 can be vented without contaminating the interior of the container 20 or any article contained inside the container 20.

The term filter 72 is not meant to be limited to a fibrous material. The term is meant to broadly describe any material which is permeable to gases but impermeable to microorganisms. For example, the term filter 72 in this application may describe something as simple as CSR wrap or TJYEK™, which are both materials which are gas permeable but impermeable to microorganisms. Alternatively, the filter 72 can be a conventional fibrous filter which excludes microorganisms.

FIG. 8 shows an embodiment of a diffusion restricted container 20 in which the diffusion restriction results from a communication port 30 comprising a substantially vertical tube 70. Preferably, there is a filter 72 inside or attached to the vertical tube 70, where the filter 72 is permeable to gases but does not allow bacteria to pass. In FIG. 8, the filter 72 is inside the substantially vertical tube 70. The filter 72 prevents microorganisms from entering the container when the system is vented after the article is sterilized. Alternatively, the gas-permeable and microorganism-impermeable filter 72 may be present in another part of the system. The diffusion restriction in the container 20 of FIG. 8 may result from the substantially vertical tube 70, the filter 72, or a combination of the substantially vertical tube 70 and the filter 72. When the diffusion restriction in the container 20 results from the vertical tube 70, the diffusion restriction in the container 20 may result from a vertical tube 70 which is at least 1.0 cm in length. The diffusion restriction in the container 20 may also result from an entry/exit port which has an internal diameter of 9 mm or less or a cross sectional area of 63.62 mm² or less.

FIG. 9 shows an alternative embodiment of a diffusion-restricted container in which the communication port 30 comprises a substantially horizontal tube 74 with a filter 72, where the filter 72 is permeable to gases but impermeable to microorganisms. A first end of the substantially horizontal tube 74 is open to the interior of the container 20, and a second end of the substantially horizontal tube 74 is open to the environment outside the diffusion-restricted container 20. The diffusion restriction in the container 20 may result from the substantially horizontal tube 74, the filter 72, or a combination of the substantially horizontal tube 74 and the filter 72. The diffusion restriction in the container 20 may also result from an entry/exit port, where the entry/exit port is at least 1.0 cm in length or having an internal diameter of 9 mm or less or has a cross sectional area of 63.62 mm² or less. The entry/exit port can be in any angle relative to the container.

Figure 10:
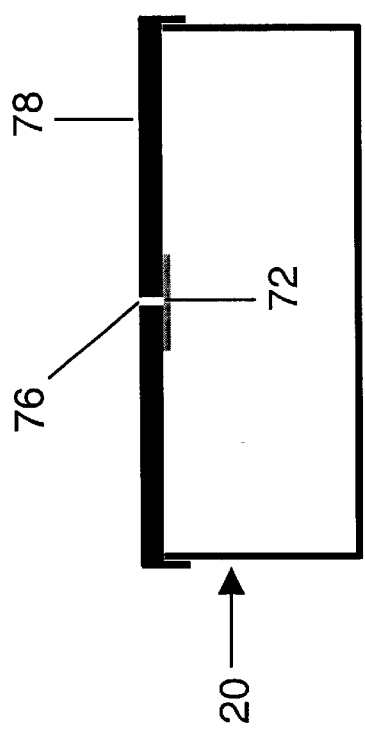
FIG. 10 is a cross-sectional illustration of one embodiment of a diffusion restricted environment represented by a container with a hole on the container as a limited diffusion port, where the lid of the container is thicker in the area of the hole than in the remainder of the lid.
Figure 11:
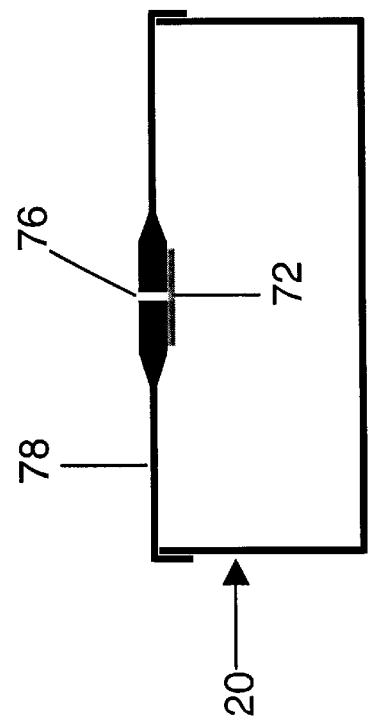
FIG. 11 is a cross-sectional illustration of one embodiment of a diffusion restricted environment represented by a container having a hole as a limited diffusion port, where the lid has an even thickness.

FIGS. 10 and 11 show embodiments of diffusion restricted containers in which the diffusion restriction results from a hole 76 as the communication port. The diffusion restriction in the container 20 may result from a hole 76 which has an internal diameter of 9 mm or less or a hole 76 with an area of 63.62 mm² or less or from a hole 76 which has a length of 1.0 cm or more. In the embodiment shown in FIG. 10, a lid 78 on the container 20 is thicker in the region of the hole 76 than in the remainder of the lid 78. The hole 76 is therefore like a vertical entry/exit port, with a longer length than if the lid 78 were of uniform thickness. A filter 72 preferably covers the hole 76, where the filter 72 is permeable to gases but impermeable to microorganisms to prevent bacteria from entering the hole 76 when the system is vented after sterilization has occurred. The diffusion restriction in the container 20 may result from the hole 76, the filter 72, or a combination of the hole 76 and the filter 72. If the diffusion restriction results from the hole 76, the diffusion restriction in the container 20 may result from a hole 76 which is at least 1.0 cm long, has an area of 63.62 mm$^2$ or less, or which has a diameter of 9 mm or less. The filter 72 may be located above the hole 76, inside the hole 76, or underneath the hole 76. In FIG. 10, the filter 72 is below the hole 76.

In FIG. 11, the diffusion-restricted container 20 comprises a lid 78 of uniform thickness with a communication port comprising a hole 76. A gas permeable and microorganism impermeable filter 72 preferably covers the hole 76. The diffusion restriction in the container 20 of FIG. 11 may result from the hole 76, the filter 72, or a combination of the hole 76 and the filter 72. If the diffusion restriction in the container 20 of FIG. 11 results from the hole 76, the lid 78 may have a thickness of 1.0 cm or more, so that the hole 76 in the lid 78 has a length of at least 1.0 cm. Alternatively, the hole 76 may have a diameter of 9 mm or less or an area of 63.62 mm$^2$ or less. In another embodiment, the diffusion restriction in the container results from a combination of the hole 76 and the filter 72. The filter 72 may be located inside the hole 76, above the hole 76, or below the hole 76. In FIG. 11, the filter 72 is below the hole 76.

Figure 12:
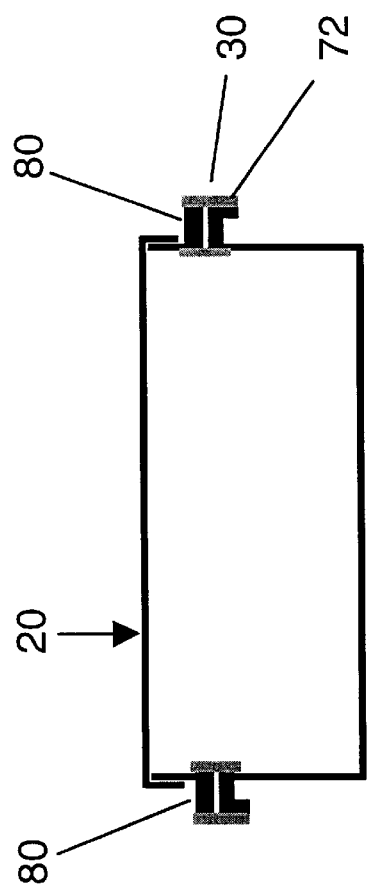
FIG. 12 is a cross-sectional illustration of one embodiment of a diffusion restricted environment represented by a container having an open channel in the handle of the container with a gas permeable and microorganism impermeable filter covering the channel as a limited diffusion port.

The embodiment of the diffusion-restricted container 20 shown in FIG. 12 comprises at least one handle 80. The handle 80 of FIG. 12 comprises a communication port 30 passing from the outside to the inside of the container 20 through the handle 80. Although the embodiment shown in FIG. 12 comprises two handles 80 where both handles 80 have communication ports 30, both the second handle 80 and the second communication port 30 are optional. For example, the container may have two handles 80 but only one communication port 30. Preferably, there is at least one gas permeable and microorganism impermeable filter 72 covering the communication port 30 in the handle 80 to prevent bacteria from entering the diffusion-restricted container 20 after the devices in the container 20 have been sterilized. In the embodiment shown in FIG. 12, there are two filters 72 on each communication port 30. In other embodiments, there is only one filter 72 on each communication port 30. The filter 72 can also be located in the communication port 30. The diffusion restriction in the embodiment of the diffusion restricted container 20 shown in FIG. 12 may be due to the communication port 30, the filter 72, or a combination of the communication port 30 and the filter 72.

Figure 13:
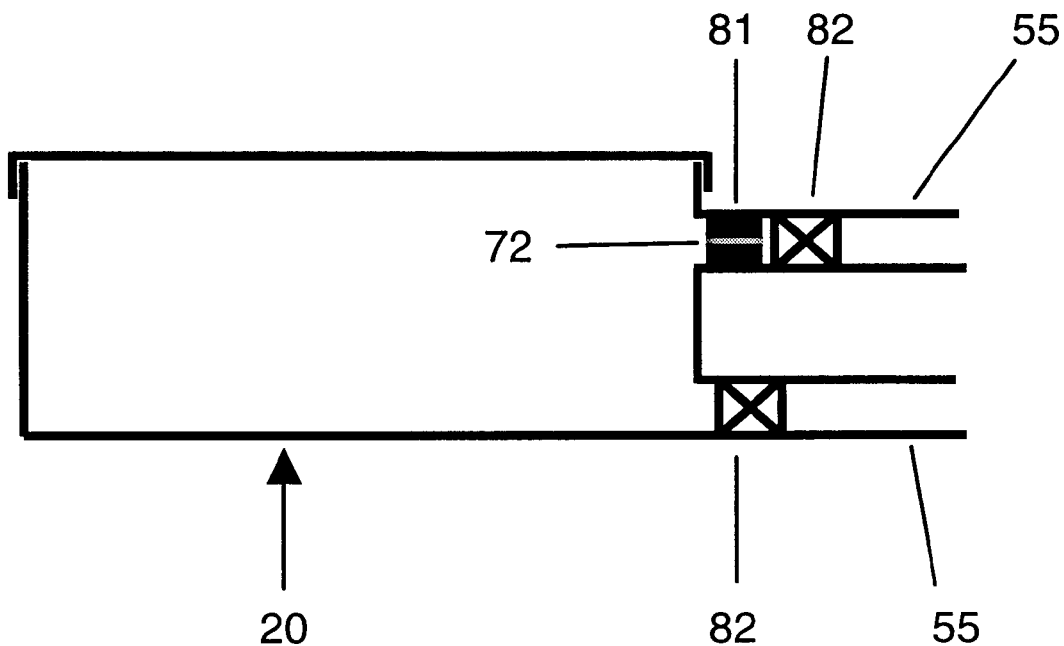
FIG. 13 is a cross-sectional illustration of one embodiment of a diffusion restricted environment represented by an attachable/detachable container having a diffusion restricted port with a gas permeable and microorganism impermeable filter and a valve and a second port with a valve.
Figure 14:
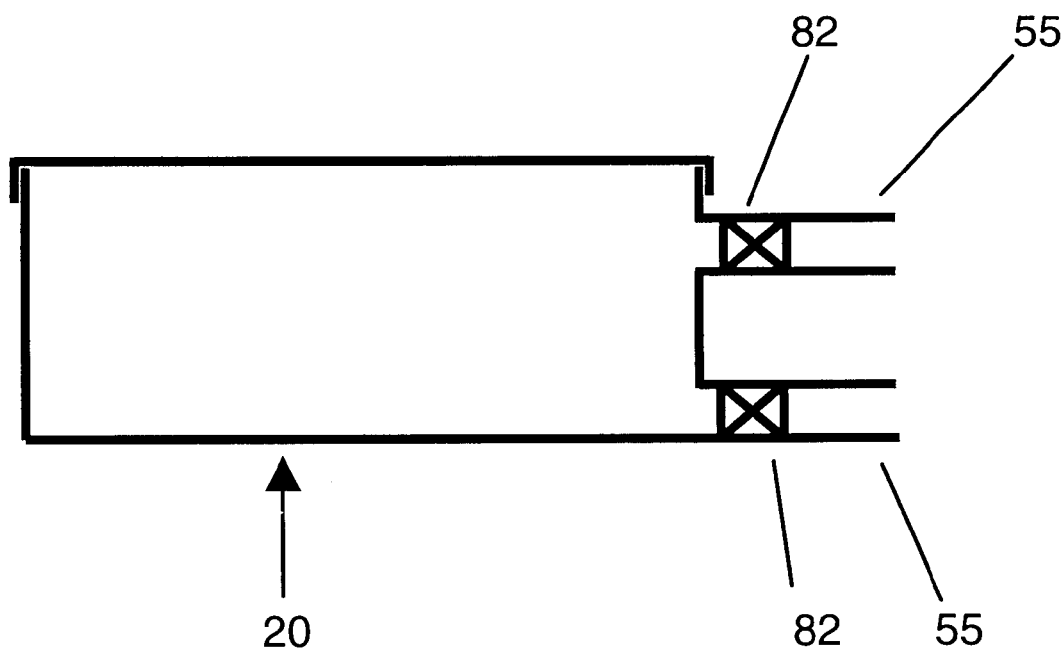
FIG. 14 is a cross-sectional illustration of one embodiment of a diffusion restricted environment represented by an attachable/detachable container having two ports with valves.

FIGS. 13 and 14 show two embodiments of attachable/detachable containers 20 as alternative embodiments of diffusion-restricted containers suitable for use in various embodiments of the method of the invention. In the embodiment of the attachable/detachable container 20 shown in FIG. 13, the container 20 comprises two ports 55. In other embodiments of the attachable/detachable container 20, only one port 55 is present. In the embodiment shown in FIG. 13, a first port 55 comprises a reducer 81, where the reducer 81 reduces the diameter of the port 55. The reducer 81 may be of any shape. The reducer 81 of FIG. 13 is shaped like a cylinder with a hole along the length of the cylinder. A gas-permeable and microorganism-impermeable filter 72 is located inside the bore of the reducer 81. Although the embodiment of the first port 55 shown in FIG. 13 additionally comprises a valve 82, the valve 82 is optional. The diffusion restriction in the container 20 of FIG. 13 may result from the port 55, the reducer 81, the filter 72, the valve 82, or any combination of the port 55, the reducer 81, the filter 72, and the valve 82. In some embodiments, the port 55 or the reducer 81 is at least 1.0 cm in length, acting as an entry/exit port and creating diffusion restriction in the container 20. In other embodiments, the port 55 or reducer 81 has a diameter of 9 mm or less or has an area of 63.62 mm$^2$ or less, acting as an entry/exit port and creating diffusion restriction in the container 20. In the embodiment of the attachable/detachable container 20 shown in FIG. 13, there is a second port 55 with a valve 82. The second port 55 can be used to create diffusion restriction instead of the first port 55. Optionally, the valve 82 may comprise a gas permeable and microorganism impermeable filter. The filter may be in the bore of the valve 82 or in the port 55. The filter prevents microorganisms from entering the container 20 when the system is vented. In an alternative embodiment, the gas permeable and microorganism impermeable filter is present elsewhere in the system.

In the embodiment of the attachable/detachable container 20 shown in FIG. 14, the container 20 comprises two ports 55 and two valves 82. Optimally, the valve 82 further comprises a gas permeable and microorganism impermeable filter in the bore of the valve 82. The diffusion restriction in the attachable/detachable container 20 shown in FIG. 14 may be due to the valve 82, the filter, or a combination of the valve 82 and the filter. Although the embodiment shown in FIG. 14 shows two ports 55 with two valves 82, the second port 55 and valve 82 are optional. Either, or both, of the two valves 82 can create the diffusion restriction.

Figure 15:
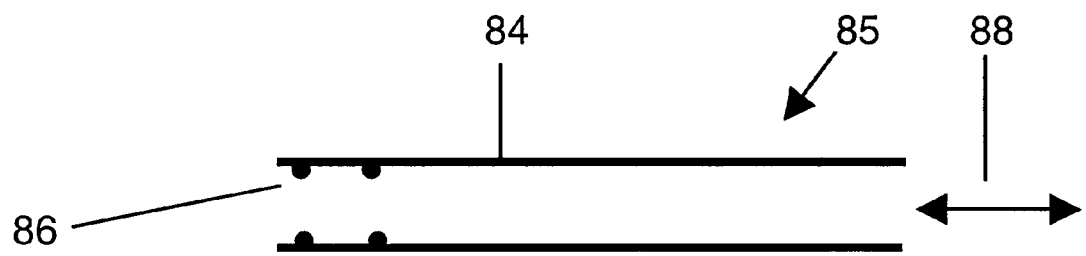
FIG. 15 is a cross-sectional illustration of a connector with O-rings for connecting an attachable/detachable container to a source of vacuum, source of fluid, and or other feedthrough.
Figure 16:
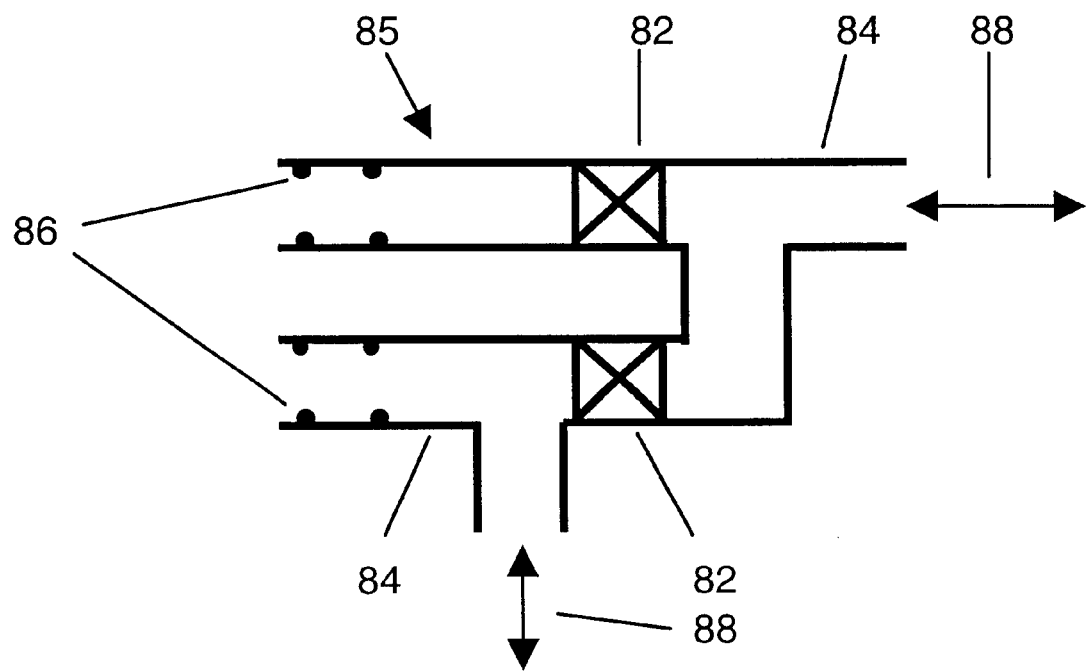
FIG. 16 is an cross-sectional illustration of an alternative embodiment of a connector for connecting an attachable/detachable container to a source of vacuum, source of fluid, and/or other feedthrough, where the connector allows attachment of one or two ports.

FIGS. 15 and 16 show embodiments of suitable connectors 85 for connecting the attachable/detachable containers 20 shown in FIGS. 13 and 14 to a source of vacuum, fluid and/or other feedthrough 88. FIG. 15 shows a tube 84 with a plurality of O-rings 86 on the inside of one end of the tube 84. The O-rings are preferably made of a material which is resistant to degradation by hydrogen peroxide. Suitable materials for fabricating the O-rings include, but are not limited to VITON™, TEFLON™, or silicone. In some embodiments, there is only one O-ring 86 inside of the tube 84. The second end of the tube 84 is connected to a source of vacuum, fluid, and/or other feedthrough 88. The fluid can be a liquid or a gas. In an embodiment, the fluid comprises peroxide, preferably hydrogen peroxide or peracetic acid.

FIG. 16 shows an alternative embodiment of a connector 85 for connecting the attachable/detachable containers 20 of FIGS. 13 and 14 to the source of vacuum, fluid, and/or other feedthrough 88. The embodiment of the connector 85 shown in FIG. 16 comprises two tubes 84 with two valves 82. The tubes 84 comprise a plurality of O-rings 86 inside a first end. The embodiment of the connector 85 shown in FIG. 16, further comprises two sources of vacuum, sources of fluid, and/or other feedthrough 88. The two tubes 84 and two sources of vacuum, fluid, and/or other feedthrough 88 can operate independently of one another by closing one or both valves 82. In other embodiments of the connector, only one valve 82 and one source of vacuum, fluid, and/or other feedthrough 88 are present.

FIGS. 17–20 show various embodiments of attachable/detachable containers 20 connected to the connector 85 of FIG. 15. In the embodiment shown in FIG. 17, an attachable/detachable container 20 with a single port 55 comprising a reducer 81 with a filter 72 in the bore of the reducer 81 is attached to the connector 85 of FIG. 15 by connecting the port 55 of the attachable/detachable container 20 to the tube 84 of the connector 85. The O-rings 86 inside the tube 84 create an air-tight seal between the port 55 and the tube 84. In the embodiment of the attachable/detachable container 20 shown in FIG. 17, the diffusion restriction in the container 20 is created by the port 55, the reducer 81, the filter 72, or any combination of the port 55, the reducer 81, and the filter 55.

Figure 17:
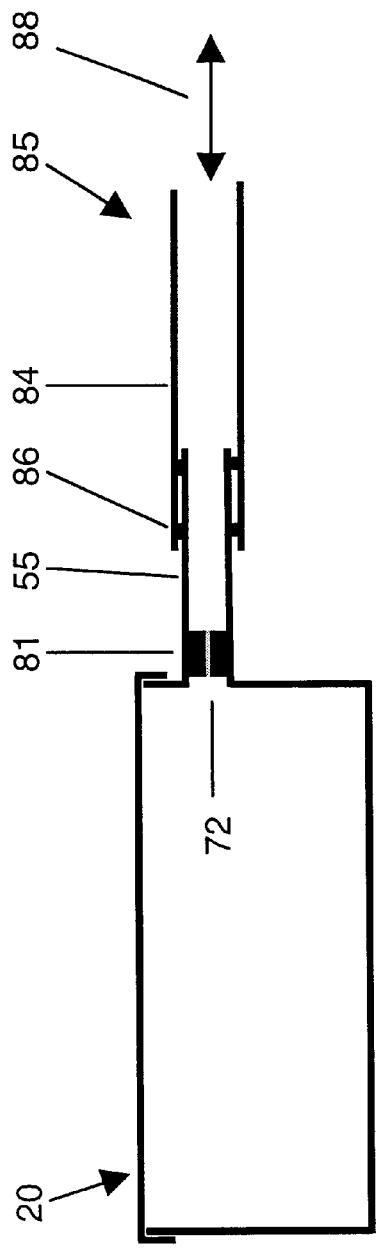
FIG. 17 is a cross-sectional illustration of an attachable/detachable container with a port with a gas permeable and microorganism impermeable filter attached to the connector of FIG. 15.
Figure 18:
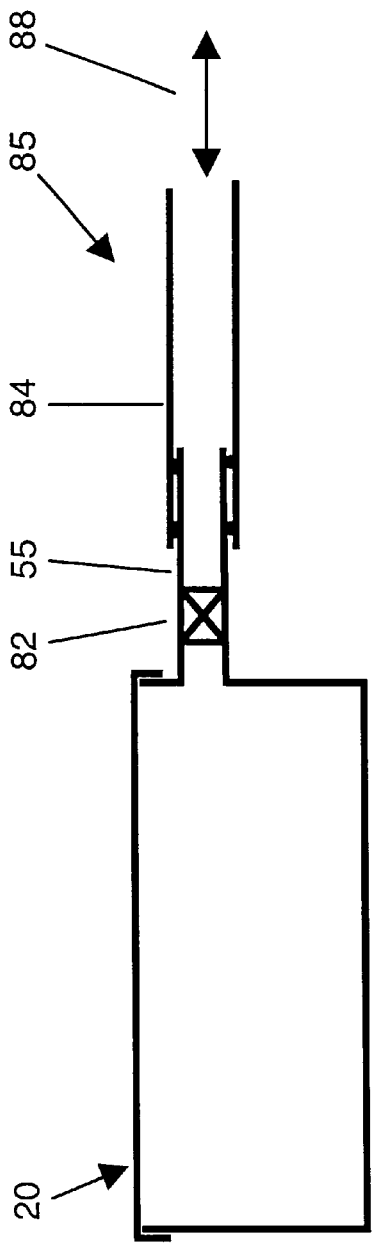
FIG. 18 is a cross-sectional illustration of an attachable/detachable container with a valve attached to the connector of FIG. 15, where the valve on the attachable/detachable container acts as the diffusion-restricted port.

The embodiment shown in FIG. 18 is similar to that shown in FIG. 17, except that the attachable/detachable container 20 has a port 55 with a valve 82 rather than a reducer 81 and a filter 72, as in the embodiment shown in FIG. 17. The attachable/detachable container 20 of FIG. 18 is attached to the connector 85 shown in FIG. 15. The valve 82 may also have a filter in the bore of the valve. The diffusion restriction in the attachable/detachable container of FIG. 18 may be due to the port 55, the valve 82, the filter, or any combination of the port 55, the filter, and the valve 82.

Figure 19:
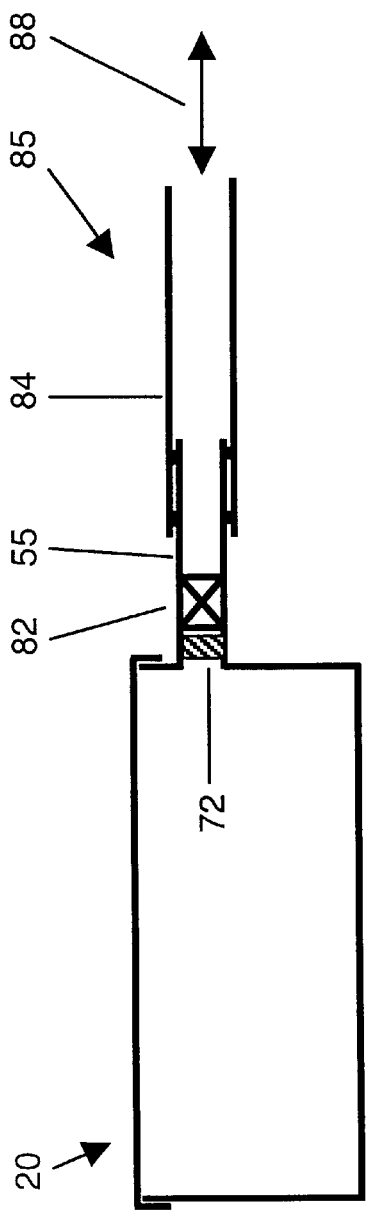
FIG. 19 is a cross-sectional illustration of an attachable/detachable container with a valve and a gas permeable and microorganism impermeable filter attached to the connector of FIG. 15, where the valve and/or the filter on the attachable/detachable container act as the diffusion-restricted port.

In the embodiment shown in FIG. 19, the attachable/detachable container 20 has a port 55 with a filter 72 and a valve 82. The attachable/detachable container 20 is attached to the connector 85 of FIG. 15. The diffusion restriction in the attachable/detachable container 20 may be due to the valve 82, the filter 72, or the combination of the valve 82 and the filter 72. The filter 72 is permeable to gases but impermeable to microorganisms, so that the attachable/detachable container 20 may be vented after sterilization without recontaminating the interior of the attachable/detachable container 20 or any article contained in the attachable/detachable container 20.

Figure 20:
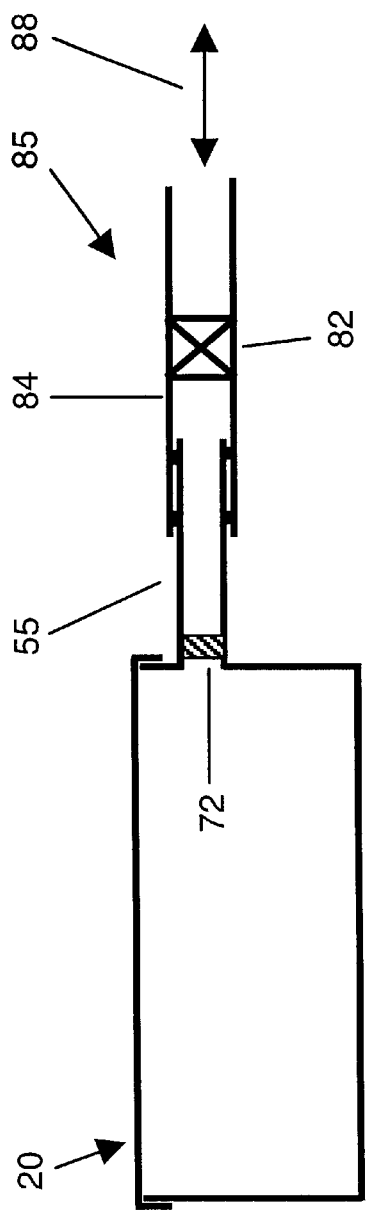
FIG. 20 is a cross-sectional illustration of an attachable/detachable container with a gas permeable and microorganism impermeable filter attached to the connector of FIG. 15, where the filter on the container and/or the valve on the container act as the diffusion-restricted port.

FIG. 20 shows a attachable/detachable container 20 comprising a filter 72. The attachable/detachable container 20 is attached to a connector 85 similar to the connector 85 of FIG. 15, except that the connector 85 in FIG. 20 also comprises a valve 82. The valve 82 of the connector 85 is located between the attachable/detachable container 20 and the source of vacuum, fluid, and/or other feedthrough 88. In the embodiment shown in FIG. 20, the attachable/detachable container 20 may be vented from the source of vacuum, fluid, and/or other feedthrough 88 by opening the valve 82 on the connector 84. The diffusion restriction in the attachable/detachable container 20 may be due to the valve 82, the filter 72, or the combination of the valve 82 and the filter 72. The filter 72 is preferably permeable to gas but impermeable to microorganisms, so that the attachable/detachable container 20 and any article inside the container 20 are not recontaminated when the attachable/detachable container 20 is vented.

Figure 21:
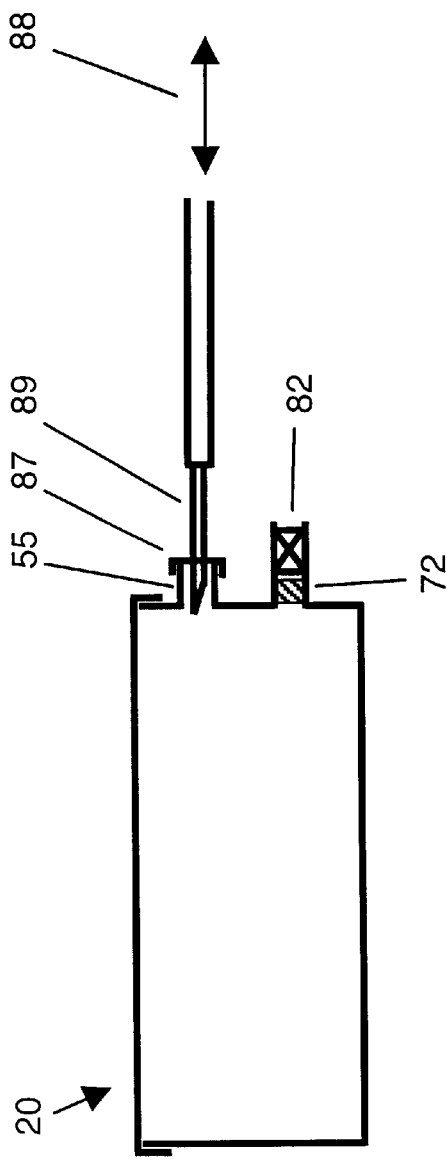
FIG. 21 is a cross-sectional illustration of an attachable/detachable container with two ports, one port with a valve and a gas permeable and microorganism impermeable filter and the second port with a septum, where the septum is punctured by a needlelike device connected to a vacuum source.

The attachable/detachable container 20 shown in FIG. 21 has two ports 55. A first port 55 is equipped with a filter 72 and a valve 82. A second port 55 has a septum 87. The septum 87 is made of flexible plastic or rubber which is impermeable to gases, so that the attachable/detachable container 20 may be evacuated. It is preferred that the plastic or rubber making up the septum 87 is resistant to hydrogen peroxide. Examples of materials suitable for forming the septum include, but are not limited to, VITON™ or silicone. In FIG. 21, the septum is punctured by a needlelike device 89 which is connected to the source of vacuum, fluid, and/or other feedthrough 88. In this embodiment, the diffusion restriction in the attachable/detachable container 20 may be due to the needlelike device 89 which is acting as an entry/exit port. The entire sterilization process may occur through the needlelike device 89 as the entry/exit port. If the diffusion restriction in the container 20 is due to the needlelike device 89, the diffusion restriction may result from a needlelike device 89 which is at least 1.0 cm in length, has an internal diameter of 9 mm or less, or has a cross sectional area of $63.62 \text{ mm}^2$ or less.

The first port 55 of the attachable/container 20 shown in FIG. 21 may optionally be attached to a connector 85 which is attached to the source of vacuum, fluid, and/or other feedthrough 88. In this embodiment, the diffusion restriction in the attachable/detachable container may be due to the port 55, the filter 72, the valve 82, or any combination of the port 55, the filter 72, and the valve 82. The sterilization of the attachable/detachable container 20 may then occur through the first port 55 having the valve 82 and the filter 72.

Figure 22:
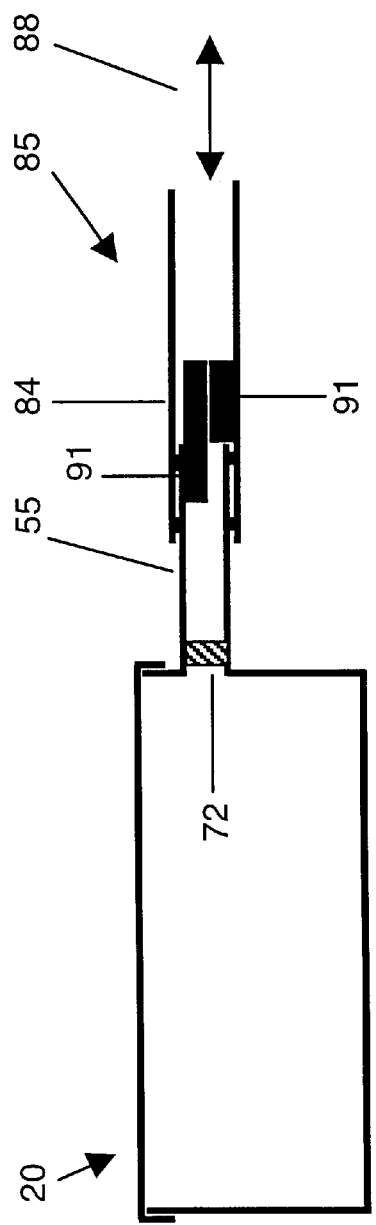
FIG. 22 is a cross-sectional illustration of an attachable/detachable container attached to a connector, where the port on the container has a gas permeable and microorganism impermeable filter and where the diffusion restriction in the container is due to a combination of the container and the connector.

FIG. 22 shows an attachable/detachable container 20 where the port 55 has a filter 72 and a restrictor 91. The filter 72 is permeable to gases but impermeable to microorganisms. The attachable/detachable container 20 is attached to a connector 85 which is connected to the source of vacuum, fluid, and/or other feedthrough 88. The connector 85 also has a restrictor 91. In some embodiments, neither the port 55 with the restrictor 91 nor the connector 85 with the restrictor 91 in the connector 85 alone causes diffusion restriction in the attachable/detachable container 20. When the attachable/detachable container 20 with the port 55 with the restrictor 91 is attached to the connector 85 with the restrictor 91, however, the two restrictors 91 fit together closely enough that the combination of the port 55 with its restrictor 91 and the connector 85 with its restrictor 91 leads to diffusion restriction in the container 20. In this embodiment, neither the port 55 and its restrictor 91 nor the connector 85 with its restrictor 91 alone cause the diffusion restriction.

Figure 23:
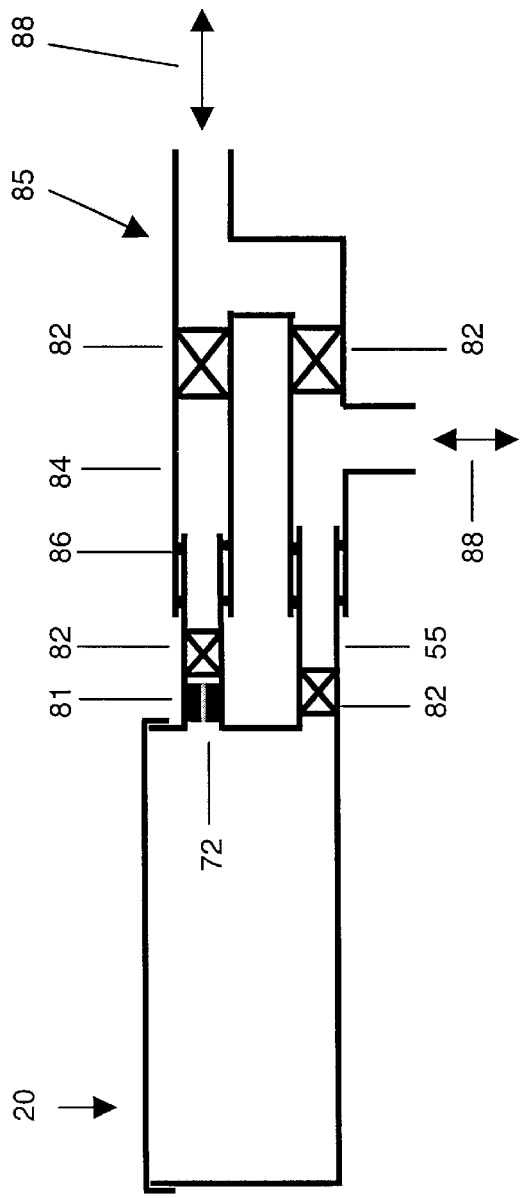
FIG. 23 is a cross-sectional illustration of an attachable/detachable container with two ports attached to the connector of FIG. 16, where one port on the attachable/detachable container has a gas permeable and microorganism impermeable filter and a valve and a second port has a valve.

In the embodiment shown in FIG. 23, the attachable/detachable container 20 of FIG. 13 is attached to the connector 85 of FIG. 16. The O-rings 86 on the connector 85 form a vacuum-tight seal with the port 55 of the attachable/detachable container 20. The diffusion restriction in the attachable/detachable container 20 in FIG. 23 can be caused by the port 55, the reducer 81, the filter 72, the valve 82 in the top port 55, the valve 82 in the connector 85, or a combination. Alternatively, or in addition, the diffusion restriction in the attachable/detachable container 20 can be caused by the valve 82 in the bottom port 55 in FIG. 23. The attachable/detachable container 20 can be exposed to the source of vacuum, fluid, or other feedthrough 88 through the source 88 on the right side of FIG. 23 or the source 88 at the bottom of FIG. 23.

Figure 24:
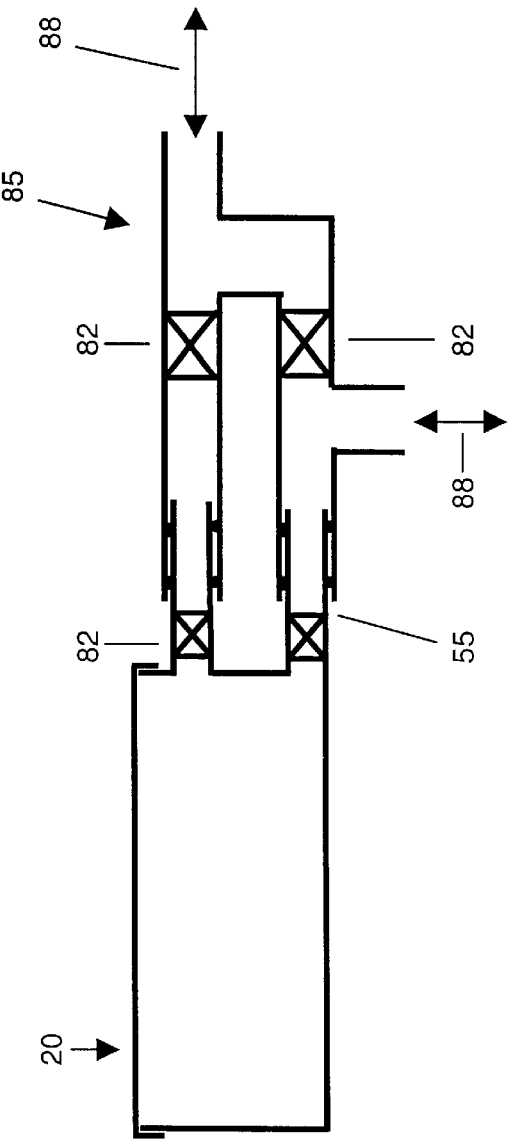
FIG. 24 is a cross-sectional illustration of an attachable/detachable container with two ports with valves attached to the connector of FIG. 16.

FIG. 24 shows the attachable/detachable container 20 of FIG. 14 attached to the embodiment of the connector 85 of FIG. 16. The diffusion restriction in the attachable/detachable container 20 can be caused by either or both ports 55 and/or any of the valves 82. The source of vacuum, source of fluid, or other feedthrough 88 can be either the source 88 at the right of FIG. 24 or the source 88 at the bottom of FIG. 24. In other embodiments, an attachable/detachable container 20 having only one port 55 may be attached to one of the two tubes 84 of the embodiment of the connector 85 shown in FIG. 16.

It is to be understood that the embodiments shown in FIGS. 17–24 are meant to be illustrative of various embodiments, and the invention is not limited to the embodiments shown in these Figures. Other combinations of attachable/detachable containers 20 and connectors 85 can be used as alternative embodiments of the apparatus and the method of the invention. For example, the tube 84 can be smaller than the port 55, and the tube 84 may be inserted into the port 55 with the O-rings on the outside of the tube 84.

Articles may be sterilized with the embodiments of the attachable/detachable container 20 and connectors 85 shown in FIGS. 13–24 in several embodiments of the method of the invention. An article to be sterilized is placed into one of the embodiments of the attachable/detachable container 20. A liquid solution comprising vaporizable germicide, for example, a source of peroxide, such as hydrogen peroxide or peracetic acid, is placed inside the attachable/detachable container 20 or is placed in contact with the article to be sterilized in the attachable/detachable container 20. Either before or after the source of peroxide is contacted with the attachable/detachable container 20, the attachable/detachable container 20 is attached to the connector 85, where the connector 85 is in fluid communication with the source of vacuum, fluid, and/or other feedthrough 88.

The pressure in the attachable/detachable container 20 is reduced to vaporize at least a portion of the vaporizable germicide, sterilizing the article to be sterilized. Plasma may optionally be generated and contacted with the article to be sterilized. The attachable/detachable container 20 is vented with a gas. The venting comprises passing the gas through a gas permeable and microorganism impermeable filter 72, where the filter is located either on the attachable/detachable container 20 or in another part of the system. By venting the attachable/detachable container 20 through a gas permeable and microorganism impermeable filter, the sterilized article in the attachable/detachable container 20 is not reexposed to microorganisms during the venting.

The attachable/detachable container 20 may be detached from the connector 85 either before or after venting. If the attachable/detachable container 20 is separated from the connector 85 before venting, it is generally preferred that the attachable/detachable container 20 comprise at least one valve 82 and that the valve 82 be closed before the attachable/detachable container 20 is separated from the connector 85.

The attachable/detachable container 20 with the enclosed sterilized article may optionally be transported. If the valve 82 on the attachable/detachable container 20 is closed, the article in the attachable/detachable container 20 can remain sterile for extended periods of time, because the valve 82 isolates the article from the environment.

In an embodiment of the method of the invention, an article is sterilized in an attachable/detachable container 20 comprising a valve 82, and the valve 82 is closed before detaching the attachable/detachable container 82 from the connector 85 and the source of vacuum, fluid, and/or other feedthrough 88. In an embodiment, the pressure inside the attachable/detachable container 20 after closing the valve 82 and after detaching from the connector 85 is less than atmospheric pressure. The valve 82 may be controlled manually or electronically.

If the attachable/detachable container 20 containing the sterilized article is stored for extended periods of time, it is possible that a leak could occur, potentially causing contamination of the sterilized article. If the pressure inside the attachable/detachable container 20 was at less than atmospheric pressure when the valve 82 was closed, a user can test whether the attachable/detachable container leaked by listening for the sound of inflowing gas when the attachable/detachable container 20 is vented by opening the valve 82. If the attachable/detachable container 20 has leaked, the attachable/detachable container will likely be at atmospheric pressure, and the user will not hear the sound of inflowing gas when the valve 82 is opened. If no leak has occurred, the user will hear a sound when the container 20 is vented by opening the valve 82. Storing the sterilized article in an attachable/detachable container 20 at less than atmospheric pressure thus provides an opportunity to test whether the container has leaked. By passing the vent gas through a gas permeable and microbe-impermeable filter 72 during the venting, the article will not be contaminated during the testing and venting process.

In an alternative embodiment, the attachable/detachable container 20 may be pressurized to a pressure greater than one atmosphere. in this embodiment, the user will hear the sound of outflowing gas when the container 20 is vented by opening the valve 82. If no outflowing gas is heard when the valve 82 is opened, the user will know that a leak has occurred.

In another embodiment, one or more pressure measuring devices such as pressure gauges or transducers are placed on the attachable/detachable container 20. The pressure in the attachable/detachable container 20 is measured after sterilization is complete and the container 20 is sealed. If the pressure as measured by the pressure measuring device changes during storage, it may be assumed that the attachable/detachable container 20 leaked during storage.

In another embodiment, the pressure measuring device comprises a transparent valve with movable balls. The valve is attached to the attachable/detachable container 20. The transparent valve comprises two tubes, an upper tube extending upward from the center of the valve, and a lower tube extending downward from the center of the valve. Both the ends of the tubes and the portion of the tubes next to the center of the valve are constricted to an area smaller than the area of the balls, so that the balls may not pass out of the tubes or go beyond the center of the valve. If the attachable/detachable container 20 is at atmospheric pressure, both balls are at the lower ends of the respective tubes. If the attachable/detachable container 20 is above atmospheric pressure, the ball in the upper tube is forced to the top of the upper tube, next to the constriction. The ball in the lower tube is at the bottom of the lower tube, next to the constriction. If the attachable/detachable container 30 is below atmospheric pressure, both balls are forced next to the restrictions in the center of the valve.

In another embodiment, the pressure indicator comprises a receptacle with a thin film extending across the receptacle. The receptacle is attached to the attachable/detachable container 20. If the attachable/detachable container 20 is at atmospheric pressure, the film is neither dilated toward the inside nor toward the outside. If the attachable/detachable container 20 is below atmospheric pressure, the center of the film is sucked inward toward the attachable/detachable container 20. If the attachable/detachable container is above atmospheric pressure, the center of the film is pushed outward, away from the attachable/detachable container 20.

By using any of these means of measuring pressure or any other means of pressure indication, it is determined whether the attachable/detachable container 20 is above, below, or at atmospheric pressure. If the attachable/detachable container 20 was either above or below atmospheric pressure when the container 20 was stored and is at atmospheric pressure after being stored, the attachable/detachable container 20 almost undoubtedly leaked. Storing the attachable/detachable container 20 at pressures above or below atmospheric pressure with some means of determining pressure is therefore a useful way to determine whether the attachable/detachable container 20 leaked while being stored.

In an embodiment of the method of the invention, an article to be sterilized is placed in an attachable/detachable container 20, the attachable/detachable container 20 is attached to a connector 85 which is fluidly connected with the source of vacuum, fluid, and/or other feedthrough 88, and the vaporizable germicide is introduced into the attachable/detachable container 20 from the source of vacuum, fluid, and/or other feedthrough 88 rather than by contacting the attachable/detachable container 20 or the article to be sterilized with the vaporizable germicide. The attachable/detachable container 20 is then exposed to reduced pressure to vaporize the germicide, thereby sterilizing the article.

In another embodiment, an article having a diffusion restricted area is sterilized by contacting the diffusion-restricted area of the article with the vaporizable germicide, placing the article having a diffusion-restricted area into the attachable/detachable container 20, where the contacting and placing can occur in either order, and evacuating the attachable/detachable container 20 to vaporize the germicide, sterilizing the diffusion restricted area of the article. If the attachable/detachable container 20 is diffusion restricted, the exterior of the article having a diffusion restricted area is also sterilized.

Figure 25:
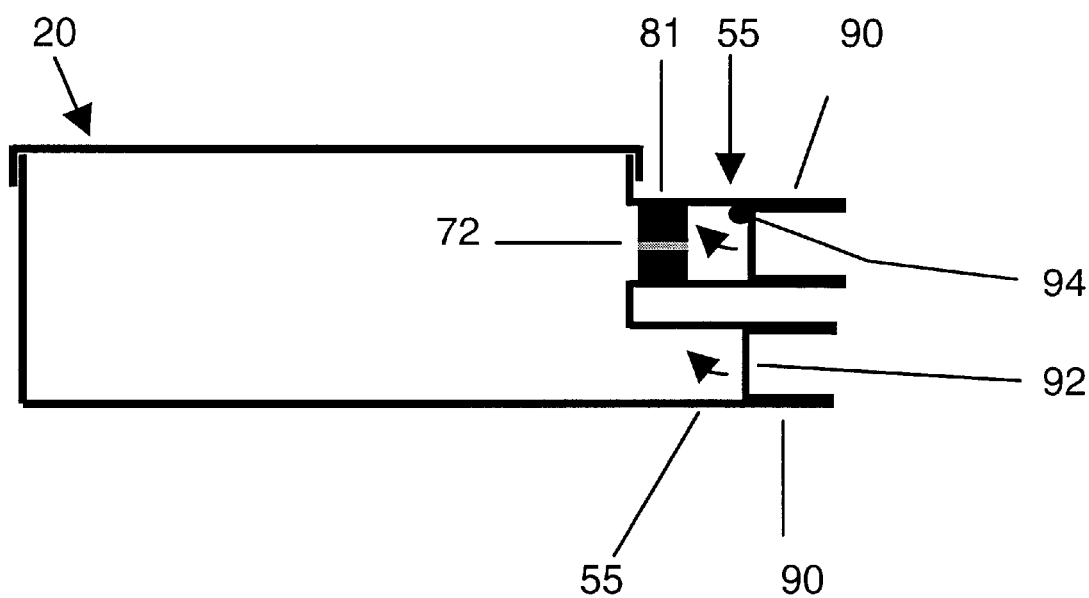
FIG. 25 is a cross-sectional illustration of an attachable/detachable container with two ports; where one port has a hinged valve and the second port has a hinged valve and a gas permeable and microorganism impermeable filter.

FIG. 25 shows an alternative embodiment of the attachable/detachable container 20 in which the attachable/detachable container 20 comprises two ports 55. The second port 55 is optional. The top port 55 in FIG. 25 is equipped with reducer 81 with a filter 72 in the bore of the reducer 81, where the filter 72 is gas permeable and microorganism impermeable. The top port 55 is also equipped with a hinged valve 90, where the hinged valve 90 comprises a flap 92 on a hinge 94, where the flap 92 has a circular shape, an oval shape, a square shape or any other shape that closes the opening in the port 55. The hinge 94 is attached to the interior of the port 55, allowing the flap 92 to open and close by swinging on the hinge 94. The flap 92 forms a gas and vacuum-tight seal with the port 55 when the flap 92 is closed. The hinged valve 90 further comprises a spring (not shown) which returns the flap 92 to a closed position when there is no external force on the flap 92 to force the flap 92 open. The hinge 94 may be either on a side of the flap 92 inside the attachable/detachable container 20 or on a side of the flap 92 outside of the attachable/detachable container 20. It is generally preferred that the hinge 94 be on the side of the flap 92 inside the attachable/detachable container 20. The second port 55 of the embodiment of the attachable/detachable container 20 shown in FIG. 25 is equipped with a hinged valve 90.

Pressurizing attachable/detachable containers 20 to pressures above atmospheric pressure after sterilization can allow for detection of leaks, because the user can hear the hiss of the gas escaping the attachable/detachable container 20 when a valve or other device is opened to vent the container 20. If there is no hiss of gas, the attachable/detachable container 20 probably leaked.

Testing for leaks by pressurizing the container 20 is advantageous with containers with hinged valves 90, because the pressurized gas in the container 20 pushes against the flap 92, sealing the flap 92 firmly in place in the port 55.

Figure 26:
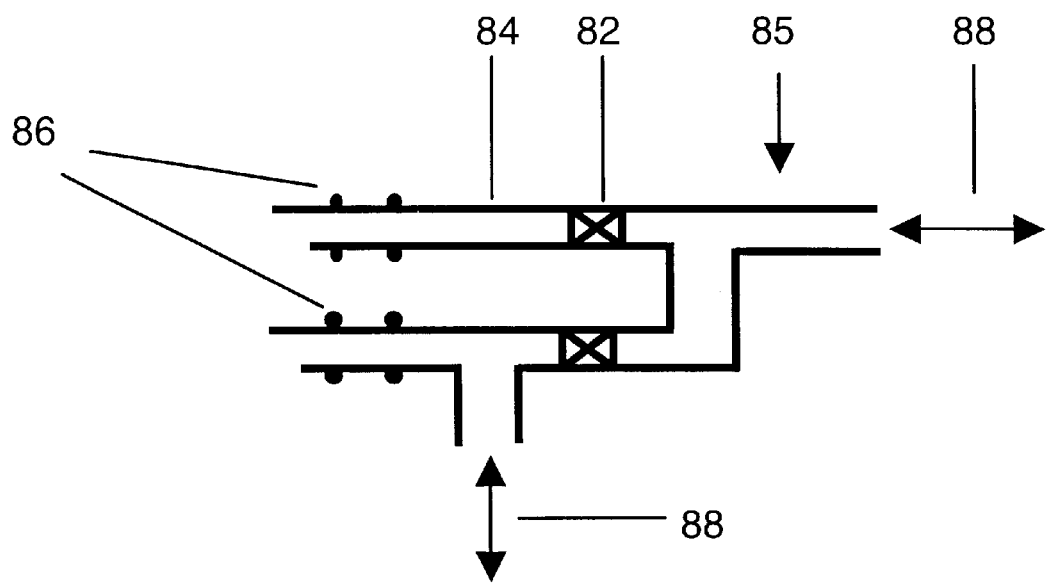
FIG. 26 is a cross-sectional illustration of a connector for connecting attachable/detachable containers with at least one port with a hinged valve to one or two sources of vacuum, fluid, or other feedthrough.

FIG. 26 shows an alternative embodiment of a connector 85. The connector 85 of FIG. 26 is essentially identical to the connector 85 of FIG. 16, with two tubes 84, two sources of vacuum, fluid, and/or other feedthrough 88, and two valves 82. In the connector 85 shown in FIG. 26 the plurality of O-rings 86 are on the outside of the tube 84 rather than on the inside of the tube 84, as in the connector 85 shown in FIG. 16. In the embodiment shown in FIG. 26, one side of the tube 84 is longer than the second side of the tube 84, so that the end of the tube 84 forms a slanted line when viewed from the side. In other embodiments, the two sides of the tube 84 are of equal length.

Figure 27:
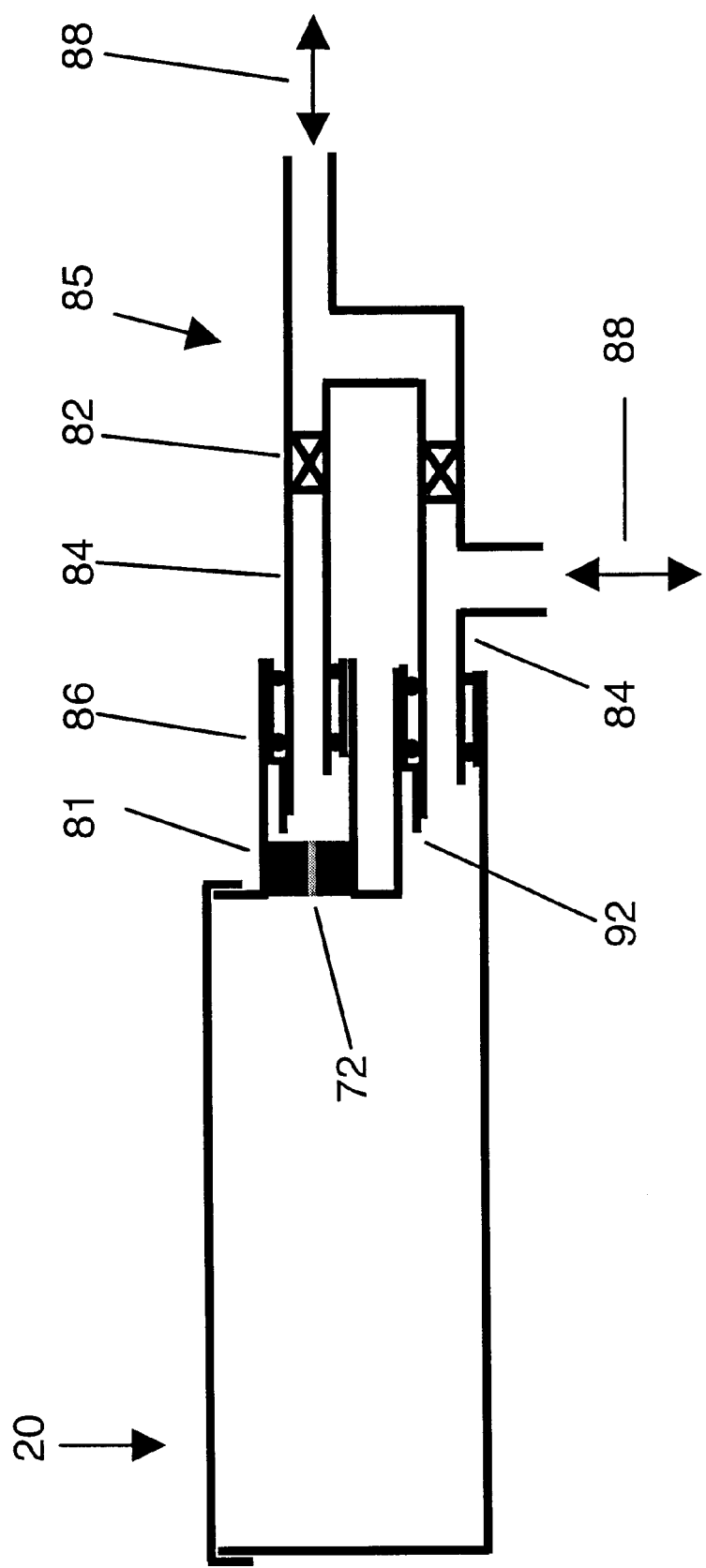
FIG. 27 is a cross-sectional illustration of the attachable/detachable container of FIG. 25 attached to the connector of FIG. 26.

FIG. 27 shows the attachable/detachable container 20 of FIG. 25 attached to the connector 85 of FIG. 26. The upper and lower tubes 84 of the connector 85 are inserted into the hinged valves 90 on the attachable/detachable container 20, opening the flaps 92 on the hinged valves 90. In the embodiment where one side of the tube 84 is longer than the second side of the tube, the longer side of the tube 84 helps to push the flap 92 aside. The plurality of O-rings 86 on the outside of the tubes 84 contact the interior of the ports 55, making a gas and vacuum-tight seal with the interior of the ports 55.

In some embodiments, there is a stop (not shown) inside one or both of the ports 55 on the attachable/detachable container 20. The stop limits the travel of the tube 84 of the connector 85 inside the port 55, so that the tube 84 does not penetrate so far into the port 55 that the O-rings 86 do not contact the inner walls of the port 55 to make the vacuum-tight seal. If the tube 84 extends too far into the port 55, the O-rings 86 would contact the flaps 92, and it is unlikely that the O-rings 86 would seal on the flaps 92. The stop can be, for example, a projection on the interior of the port 55 which contacts an end of the tube 84, limiting the travel of the tube 84 into the port 55. The optional valves 82 on the connector 85 can be used to isolate one or both of the sources of vacuum, fluid, and/or other feedthrough 88 from the attachable/detachable container 20.

After the attachable/detachable container 20 has been sterilized and vented, the connector 85 and attachable/detachable container 20 shown in FIG. 27 can be separated. When the connector 85 and the attachable/detachable container 20 of FIG. 27 are separated from one another, the flaps 92 on the hinged valves 90 close due to the force of the springs (not shown), forming an air-tight seal with the inner wall of the ports 55, isolating the interior of the attachable/detachable container 20 from the environment. The hinged valves 90 of the attachable/detachable container 20 shown in FIGS. 25 and 27 therefore provide a means of automatically isolating the interior of the attachable/detachable container 20 from the environment when the connector 85 is separated from the attachable/detachable container 20.

Figure 28:
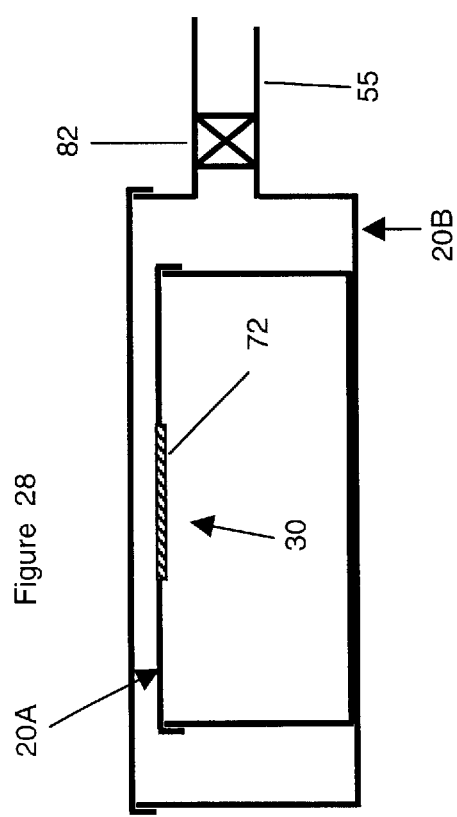
FIG. 28 is a cross-sectional illustration of a container with a gas permeable and microorganism impermeable window nested inside an attachable/detachable container with a valve.

FIGS. 28–31 show various embodiments of containers 20 contained inside attachable/detachable containers 20 as "nested containers". In FIG. 28, an inner container 20A is contained inside an attachable/detachable container 20B, where the attachable/detachable container 20B has a valve 82 on the port 55, allowing the attachable/detachable container 20B to be isolated.

The inner container 20A of FIG. 28 has a communication port 30 on the top of the container, allowing gas such as germicide vapor to pass from the inner container 20A to the inside of the attachable/detachable container 20B. The communication port 30 can be a hole, window, tube, or any other communication port 30 which allows gas or vapor to pass. Preferably, the communication port 30 is either a window which is permeable to gases but impermeable to microorganisms, or the communication port 30 is covered by a filter 72 which allows vapor to pass but does not allow microorganisms to pass. The window or filter 72 prevent microorganisms from entering the inner container 20A when the outer attachable/detachable container 20B is vented. The inner container 20A may or may not be diffusion restricted. The attachable/detachable container 20B is preferably diffusion restricted.

Figure 29:
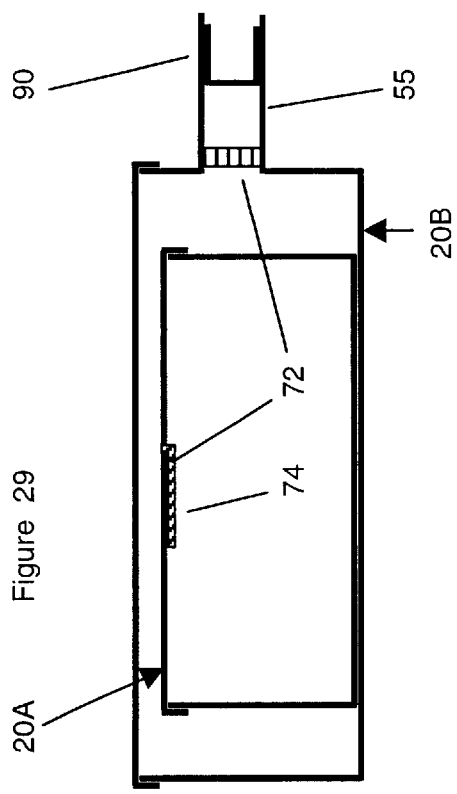
FIG. 29 is a cross-sectional illustration of a container with a substantially horizontal entry/exit port and a gas permeable and microorganism impermeable filter nested inside an attachable/detachable container with a diffusion restricted port with a hinged valve and a gas permeable and microorganism impermeable filter.

FIG. 29 shows an alternative embodiment of nested containers in which the inner container 20A has a substantially horizontal tube 74 as the communication port. Preferably, a filter 72 is placed in the horizontal tube 74, where the filter 72 is permeable to gases but impermeable to microorganisms. The horizontal tube 74 allows germicide vapor to flow from the interior of the inner container 20A to the interior of the attachable/detachable container 20B.

The attachable/detachable container 20B of FIG. 29 has a port 55 equipped with a hinged valve 90 and a filter 72, where the filter 72 is located between the hinged valve 90 and the interior of the attachable/detachable container 20B. The filter 72 is permeable to gases but impermeable to microorganisms. The filter 72 allows the attachable/detachable container 20B to be vented without contaminating the interior of the attachable/detachable container 20B or the interior and exterior of the inner container 20A.

Figure 30:
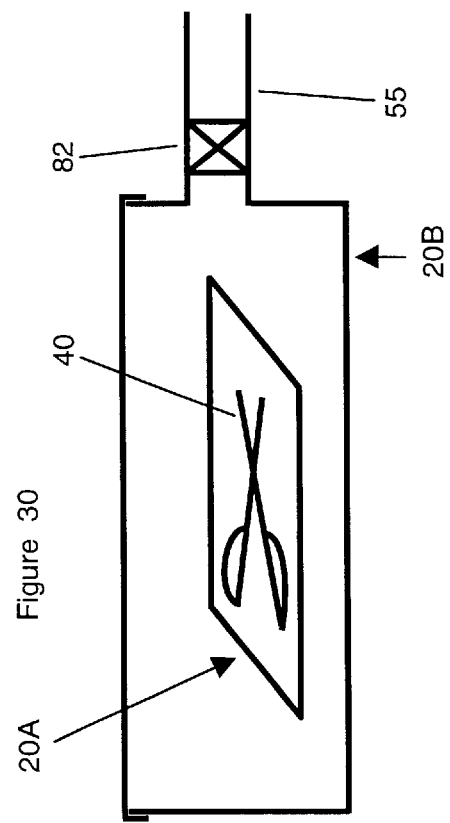
FIG. 30 is a cross-sectional illustration of a pouch containing a pair of scissors nested inside an attachable/detachable container with a valve.

FIG. 30 shows an alternative embodiment of nested containers in which the inner container 20A is a pouch. The pouch in FIG. 30 contains a non-lumen device 40, a pair of scissors. The pouch as the inner container 20A is placed inside an attachable/detachable container 20B. The attachable/detachable container 20B of FIG. 30 has a port 55 with a valve 82. The diffusion restriction in the attachable/detachable container 20B may be due to the port 55, the valve 82, or a combination of the port 55 and the valve 82. In an embodiment, at least a portion of the pouch as an inner container 20A is made of a gas permeable barrier such as TYVEK™. TYVEK™ and CSR wrap barrier are permeable to gases, including hydrogen peroxide vapor. The balance of the pouch can be made of a gas impermeable barrier such as MYLAR™.

A device to be sterilized is placed into the pouch as inner container 20A. A vaporizable germicide such as liquid comprising hydrogen peroxide is placed inside the attachable/detachable container 20B, the pouch as the inner container 20A, or both the attachable/detachable container 20B and the pouch, and a vacuum is applied to the attachable/detachable container 20B to vaporize the vaporizable germicide. The germicide vapor passes through the gas permeable portion of the pouch, either into or out of the pouch, depending on where the vaporizable germicide was placed, to sterilize the device, the interior and exterior of the pouch as an inner container 20A, and the interior of the attachable/detachable container 20B. Optionally, a plasma may be generated and flowed into the attachable/detachable container 20B. The device in the pouch can be either a non-lumen device or a lumen device. Depending on the length and internal diameter of the lumen, liquid pretreatment of the interior of the lumen may be required.

Figure 31:
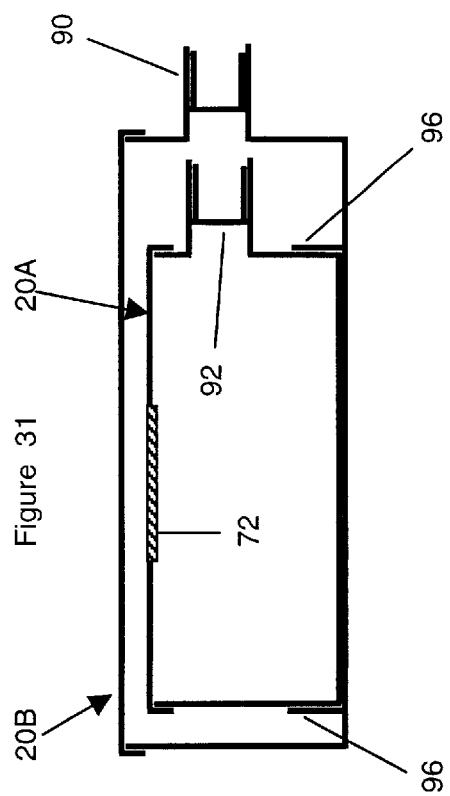
FIG. 31 is a cross-sectional illustration of a container with a gas permeable and microorganism impermeable window and a port with a hinged valve nested inside an attachable/detachable container with a hinged valve.

FIG. 31 shows an inner container 20A having a port 55 with a hinged valve 90 closed by a flap 92 attached to the inside of the port 55 with a hinge 94. The hinged valve 90 also has a spring (not shown) which forces the flap 92 closed when there is no pressure on the flap 92. The inner container 20A also has a communication port 30 on the top of the container 20A, where the communication port 30 is covered by a filter 72, where the filter 72 is permeable to gases but impermeable to microorganisms. The communication port 30 can be a hole, a tube, a window, a rectangular shaped opening, or any other opening. There is no need for the inner container 20A to be diffusion restricted.

The inner container 20A is placed in an attachable/detachable containers 20B with a hinged valve 90 on a port 55. The hinged valve 90 on the attachable/detachable container 20B is similar to the hinged valve on the inner container 20A. The communication port 30 on the inner container 20A allows vacuum or germicide vapor to be transmitted from the inside of the inner container 20A to the inside of the attachable/detachable container 20B. In the embodiment shown in FIG. 31, the inner container 20A is placed between two retaining guides 96 attached to the inside of the attachable/detachable container 20B. The retaining guides 96 fit snugly against the outside of the inner container 20A, securing and retaining the inner container 20A in a fixed position inside the attachable/detachable container 20B. The retaining guides 96 can have various shapes. In one embodiment, the retaining guides 96 are long flaps attached to the inner wall of the outer attachable/detachable container 20B. In another embodiment, the retaining guides 96 are narrow strips that fit into slots on the outside of the inner attachable/detachable container 20B. Other embodiments of retaining guides 96 will be apparent to those skilled in the art. Although the retaining guides 96 are optional, having retaining guides 96 on the inside of the attachable/container 20B is a preferred embodiment, because the retaining guides 96 hold the inner container 20A firmly in position inside the attachable/detachable container 20B.

Figure 32A:
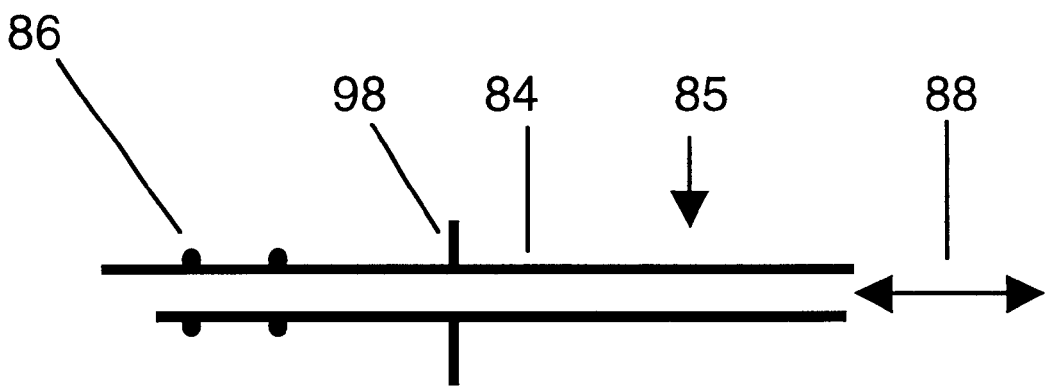
FIG. 32A a cross-sectional illustration of a connector for connecting containers with hinged valves to a source of vacuum, fluid, or other feedthrough, where the connector has a stop limiting movement of the container.

FIG. 32A shows an embodiment of a connector 85 which may be connected to the container 20B of FIGS. 29 and 31. The connector 85 comprises a tube 84 with a plurality of O-rings 86 attached to the outside of the tube 84. One end of the tube 84 is fluidly connected to a source of vacuum, fluid, and/or other feedthrough 88. The connector 85 optionally, but preferably, has a stop 98 on the outside of the tube 84. When the connector 85 is inserted into the hinged valve 90 of the attachable/detachable container 20B of FIG. 29, the stop 98 contacts the end of the port 55 and prevents the tube 84 from extending too far into the interior of the attachable/detachable container 20B. The stop 98 insures that the plurality of O-rings 86 are in the proper position to form a good seal with the inside of the port 55. If the O-rings 86 were to contact the flap 92 rather the interior of the port 55, it is probable that the O-rings 86 would not be able to form a vacuum-tight seal. The stop 98 limits the travel of the connector 85 when the stop 98 contacts the end of the port 55. The connector 85 of FIG. 32A may also be used with the attachable/detachable container 20B shown in FIG. 31 or any other container 20 having a hinged valve 90. The connector 85 of FIG. 32A may also be used with attachable/detachable containers having a valve 82 in the port 55, by inserting the tube 84 into the port 55. The O-rings 86 on the outside of the tube 84 would form a seal with the inside surface of the port 55.

Figure 32B:
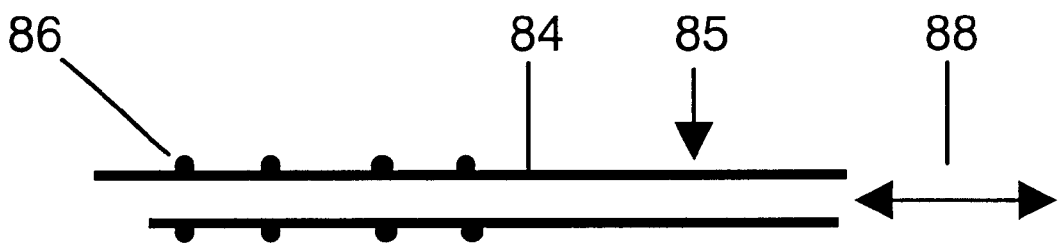
FIG. 32B is a cross-sectional illustration of a connector for connecting nested attachable/detachable containers to a source of vacuum, fluid, or other feedthrough.
Figure 33A:
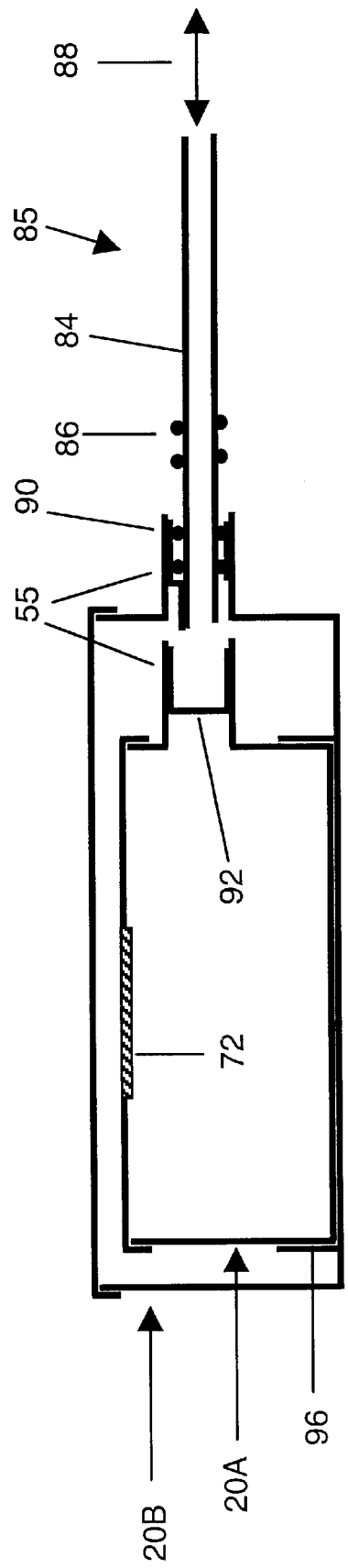
FIG. 33A is a cross-sectional illustration of the nested containers of FIG. 31 attached to the connector of FIG. 32B, where the connector extends through only one of the two hinged valves.
Figure 33B:
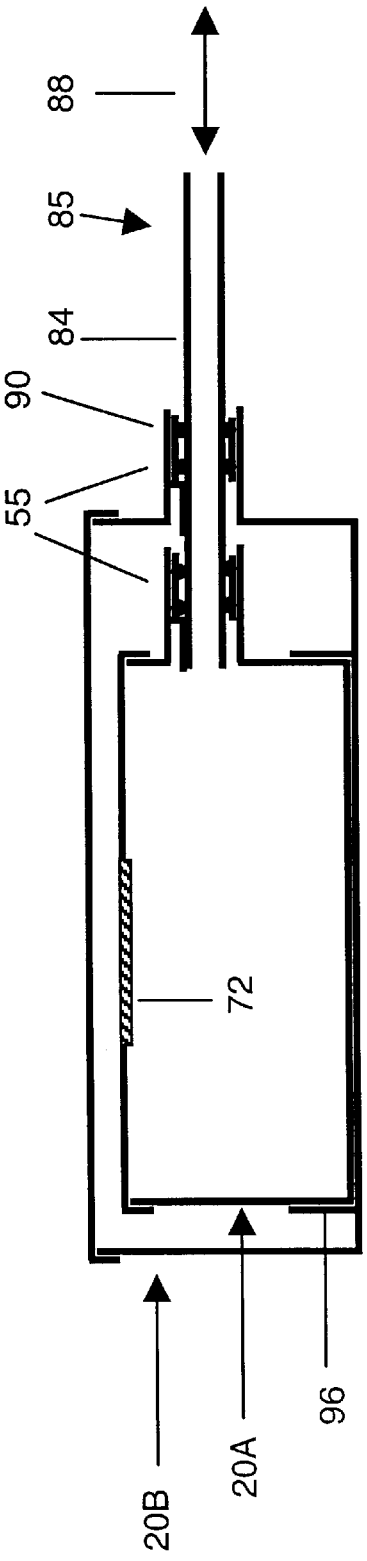
FIG. 33B is a cross-sectional illustration of the nested containers of FIG. 31 attached to the connector of FIG. 32B, where the connector extends through both of the two hinged valves.

FIG. 32B shows a connector 85 suitable for attaching to the nested containers 20A and 20B shown in FIG. 31. The connector 85 of FIG. 32B is similar to the connector 85 of FIG. 32A in comprising a tube 84 with a plurality of O-rings 86 attached to the outside of the tube 84. The connector 85 of FIG. 32B has four O-rings 86 rather than the two O-rings 86 for the connector 85 of FIG. 32A. The purpose of the four O-rings will become clear when FIGS. 33A and 33B are described. One end of the tube 84 is fluidly connected to a source of vacuum, fluid, and/or other feedthrough,88. Although the connector 85 shown in FIG. 32B does not have a stop as does the connector 85 shown in FIG. 32A, some embodiments of the connector 85 of FIG. 32A do have a stop.

Figure 32C:
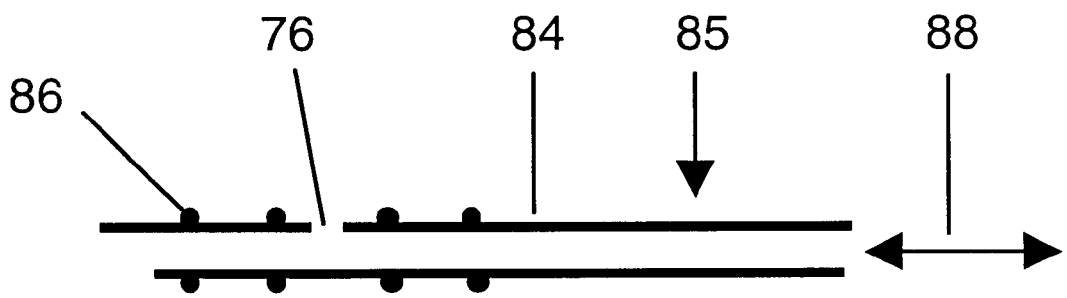
FIG. 32C is a cross-sectional illustration of a connector for connecting nested attachable/detachable containers to a source of vacuum, fluid, or other feedthrough, where the connector has an opening between the O-rings.

The connector of FIG. 32C is identical to the connector of FIG. 32B, except that there is a hole 76 in the tube 84 on the connector 85 of FIG. 32C in between the second and the third O-rings 86. The purpose of the hole 76 will be become clear when FIG. 33B is described.

The connectors 85 of FIGS. 32A, 32B, and 32C are shown with ends of one side of the tube 84 being longer than the second side of the tube 84, so that the end of the tube 84 forms a slanted line when viewed from the side. In other embodiments, the two sides of the tube 84 are of equal length.

FIGS. 33A and 33B show how the connectors 85 of FIGS. 32B or 32C attach to the nested containers 20A and 20B of FIG. 31. FIG. 33A shows the connector 85 of FIG. 32B inserted into the hinged valve 90 of the attachable/detachable container 20B of FIG. 31. When the tube 84 of the connector 85 is pushed against the flaps 92 on the hinged valve 90 of the attachable/detachable container 20B, the flap 92 is pushed aside against the force of the spring (not shown), exposing the interior of the attachable/detachable container 20B to the source of vacuum, source of fluid, and/or other feedthrough 88. The plurality of O-rings 86 on the outside of the tube 84 form a vacuum-tight seal with the inside of the port 55 of the attachable/detachable container 20B.

FIG. 33B shows how the connector 85 of either FIG. 32B or 32C can be inserted into both the hinged valve 90 of the inner container 20A and the hinged valve 90 of the attachable/detachable container 20B. When the tube 84 of the connector 85 is pushed against the flaps 92 on the hinged valve 90 of the attachable/detachable container 20B and the inner container 20A, the flaps 92 are pushed aside against the force of the spring (not shown), exposing the interior of the inner container 20A to the source of vacuum, source of fluid, and or other feedthrough 88. The plurality of O-rings 86 on the outside of the tube 84 form vacuum-tight seals with the inside of the ports 55 of the inner container 20A and the attachable/detachable container 20B. In an embodiment, there can be a stop 98 on the connector 85 as in the connector of FIG. 32A. The stop 98 on the outside of the connector 85 would contact the end of the port 55 on the attachable/detachable container 20B, limiting the movement of the tube 84 so that the O-rings 86 are in contact with the inside of the two ports 55.

The retaining guides 96 hold the inner container 20A in place inside the outer attachable/detachable container 20B when the connector 85 of FIG. 32B or FIG. 32C is pushed through the hinged valves 90. If the connector 85 of FIG. 32C is used, where there is a hole 76 between the first two and the last two O-rings 86, the hole 76 is located between the port 55 of the inner container 20A and the port 55 of the attachable/detachable container 20B after the connector 85 is inserted into the two ports 55. Although the hole 76 can be oriented in any manner, in a preferred embodiment, the hole 76 in the tube 84 is oriented upwards. If the hole 76 is oriented upwards, fluid which is introduced into the tube 84 from the source of vacuum, fluid, and/or other feedthrough 88 can travel through the tube 84 into the interior of the inner container 20A. and does not pass through the hole 76. The hole 76 on the connector 85 of FIG. 32C allows the attachable/detachable container 20B to be evacuated through the connector 85. If the connector 85 of FIG. 32C is used with the nested containers 20A and 20B shown in FIG. 31, it is not necessary to have the communication port 30 on the inner container 20A, because the inner container 20A can be evacuated through the connector 85, and the attachable/detachable container 20B can be evacuated through the hole 76 in the connector. If desired, hydrogen peroxide vapor or mist can be introduced into the inner container 20A through the connector 85 and the attachable/detachable container 20B through the hole 76 on the connector 85 of FIG. 32C. In an alternative embodiment, liquid comprising peroxide may be introduced into the inner container 20A from the source of vacuum, fluid, and/or other feedthrough 88 through the connector 85.

A general method of sterilizing articles with the nested containers 20A and 20B shown in FIGS. 28–31 is given below. The general method comprises the following:

1. An article to be sterilized is placed into the inner container 20A.

2. A vaporizable germicide is placed into the inner container 20A and/or is contacted with the article to be sterilized.

3. The inner container 20A is placed into the attachable/detachable container 20B.

4. The inner container 20A and the attachable/detachable container 20B are fluidly connected to the source of vacuum, fluid, and/or other feedthrough 88. In an embodiment, the containers 20A and 20B are fluidly connected to the source 88 though the connector 85. The operations 1, 2, 3 and 4 may be in any order. Optionally, the germicide can also be placed inside the attachable/detachable container 20B.

5. The pressure in the inner container 20A and the attachable/detachable container 20B is reduced to vaporize the germicide, sterilizing the article in the inner container 20A, the inside and the outside of the inner container 20A, and the inside of the attachable/detachable container 20B. The germicide vapor reaches the inside of the attachable/detachable container 20B through the communication port 30 in the inner container 20A.

Optionally, plasma is generated and contacted with the germicide and/or article to be sterilized and/or the two containers 20. The plasma may be generated inside one or both of the containers 20.

In an alternative embodiment, vaporizable germicide is placed into both the inner container 20A and the attachable/detachable container 20B. When the pressure in the attachable/detachable container 20B is reduced by exposing the connector 85 to a vacuum from the source of vacuum, fluid, and/or other feedthrough 88, the communication port 30 in the inner container 20A allows gas to be transferred from the inner container 20A to the attachable/detachable container 20B, reducing the pressure in the inner container 20A, vaporizing the germicide, sterilizing the article in the inner container 20A as well as the interior of the inner container 20A. In another embodiment, there is no communication port 30 in the inner container 20A, and the pressure in the attachable/detachable container 20B is reduced through the hole 76 on the connector 85 of FIG. 32C.

In another embodiment of the method, germicide such as peroxide is transferred from the source of vacuum, fluid, and/or other feedthrough through the connector 85 into the inner container 20A rather than being placed directly into the inner container 20A or being contacted with the article to be sterilized in the inner container 20A. This embodiment of the method is applicable to either embodiment of the method described earlier.

Plasma may optionally be introduced into either or both of the containers in any of the embodiments of the method of the invention.

In all of the embodiments of the method of the invention, by properly placing the germicide in the inner container 20A and/or in the attachable/detachable container 20B, the interior and the exterior of the inner container 20A, the interior of the outer attachable/detachable container 20B, and the article in the inner container 20A are all sterile.

Having nested containers containing a sterile article, where the inner container 20A is sterile on exterior and the outer attachable/detachable container 20B is sterile on the interior, is useful in a medical setting. For example, the nested containers containing the sterile article can be transferred to an area close to an operating room. The outer container 20B can be opened and the inner container 20A removed. Because the exterior of the inner container 20A is sterile, the inner container 20A containing the sterile article can be transferred into a sterile environment such as an operating room without contaminating the sterile environment. The sterile article inside the sterile inner container 20A can be removed from the container and utilized at leisure without concern about contamination from the container in which it is housed.

Figure 34C:
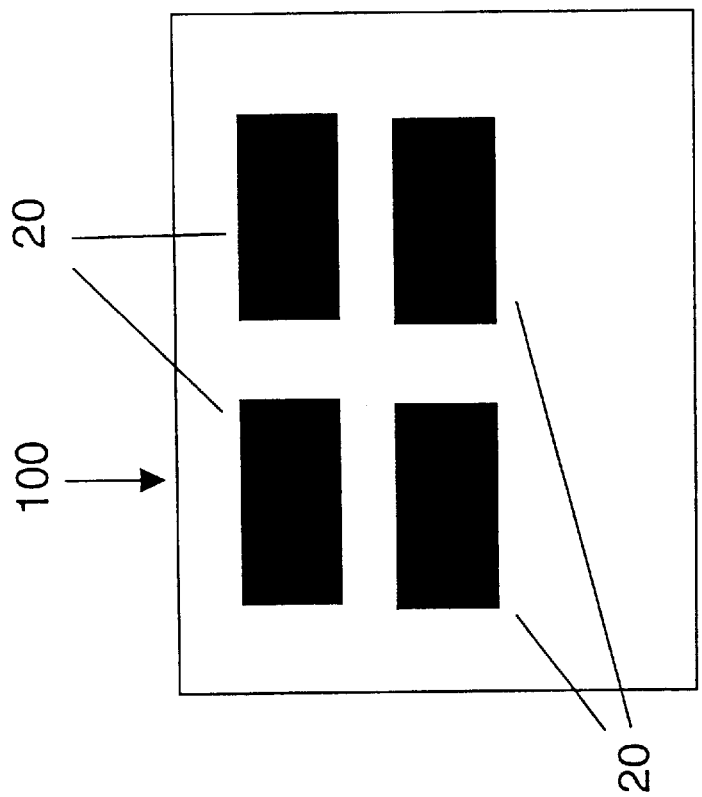
FIG. 34C is a schematic diagram of a system for sterilizing four attachable/detachable containers.
Figure 34B:
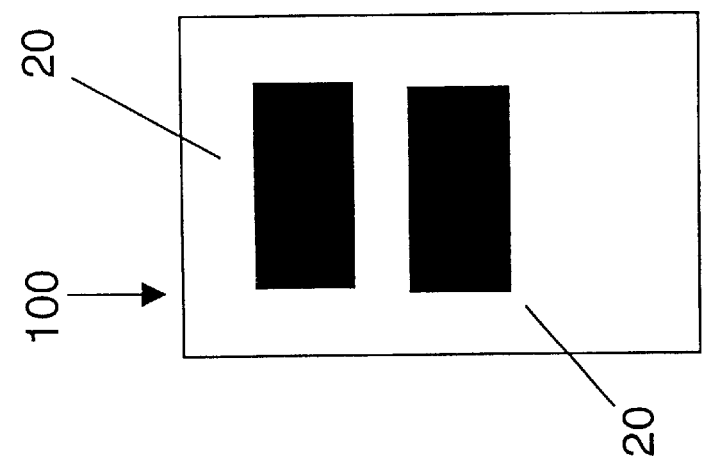
FIG. 34B is a schematic diagram of a system for sterilizing two attachable/detachable containers.
Figure 34A:
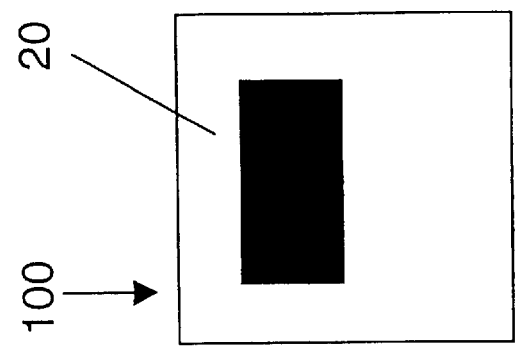
FIG. 34A is a schematic diagram of a system for sterilizing a single attachable/detachable container.

FIGS. 34A, 34B, and 34C schematically illustrate systems for sterilizing one, two, and four attachable/detachable containers, respectively. In FIG. 34A, a single attachable/detachable container 20 is attached to a system 100 for sterilizing attachable/detachable containers. The system 100 comprises a source of vacuum,, fluid, and/or other feedthrough 88. The system 100 may further comprise one or more heaters (not shown) for heating the attachable/detachable container 20 and/or a source of vaporizable germicide or peroxide (not shown). The system 100 may additionally comprise a source of plasma (not shown) and/or one or more filters (not shown), where the filters are permeable to gas and impermeable to microorganisms.

In the system 100 of FIG. 34A, the attachable/detachable container 20 is attached to the system 100. The attachable/detachable container 20 preferably contains an article to be sterilized. The attachable/detachable container 20 is in fluid communication with the system 100. Peroxide or other vaporizable germicide is placed into the interior of the attachable/detachable container 20 either before or after the attachable/detachable container 20 is attached to the system 100. The pressure in the attachable/detachable container 20 is reduced to vaporize the germicide, sterilizing the article in the attachable/detachable container 20 as well as the interior of the attachable/detachable container 20. The germicide and/or the attachable/detachable container 20 may be optionally heated. Plasma may optionally be introduced into the attachable/detachable container 20 before, during, and/or after the germicide is introduced into the attachable/detachable container 20. If the plasma is introduced prior to introducing the peroxide or germicide, the plasma helps to dry the article to be sterilized and/or the interior of the attachable/detachable container 20. If the plasma is introduced during and/or after introducing the peroxide or germicide, the plasma helps to sterilize the article inside the attachable/detachable container 20 as well as the interior of the attachable/detachable container 20. The plasma also helps to remove the residual in the container.

FIG. 34B shows a schematic diagram of a system 100 for sterilizing two attachable/detachable containers 20. The system 100 comprises a source of vacuum, fluid, and/or other feedthrough 88. In the system 100 shown in FIG. 34B, two attachable/detachable containers 20 may be sterilized simultaneously. Although in some embodiments, the system 100 for sterilizing two attachable/detachable containers 20 may comprise two separate sources of vacuum, fluid, and/or other feedthrough 88, it is in general preferred that the system 100 comprise a single source of vacuum, fluid, and/or other feedthrough 88, where the source of vacuum, fluid, and/or other feedthrough further comprises one or more valves 82 between the source of vacuum, fluid, and/or other feedthrough 88 and the attachable/detachable containers 20 so that a first attachable/detachable container 20 can be attached and detached from the system 100 without interfering with the operations which are occurring on a second attachable/detachable container 20. The system 100 may further comprise one or more heaters for heating the two attachable/detachable containers 20 and/or a source of germicide or peroxide (not shown). The system 100 may additionally comprise one or more sources of plasma (not shown). The system 100 may additionally comprise one or more filters (not shown), where the filters are permeable to gas and impermeable to microorganisms. Although not necessary, it is in general preferable that the system 100 be able to perform each of the sterilization steps on the first attachable/detachable containers 20 independently of the sterilization steps which are occurring on the second attachable container 20. The two attachable/detachable containers 20 may therefore be sterilized at different times or under different conditions.

With the system 100 of FIG. 34B, the attachable/detachable containers 20 may be sterilized independently of one another, in a synchronized manner, in an asynchonized manner, or in a multitasking manner with at least one vacuum source.

FIG. 34C shows a schematic diagram of a system 100 for sterilizing four attachable/detachable containers 20. Preferably, each of the four attachable/detachable containers 20 in the system 100 can be attached, detached, and sterilized independently. In other, less preferred embodiments, the attaching, detaching, and sterilization of each of the attachable/detachable containers 20 occurs simultaneously with the attaching, detaching, and sterilization of the other attachable/detachable containers 20. Although performing the operations on each of the attachable/detachable containers 20 simultaneously with the operations on the other containers would minimize redundant equipment, flexibility is lost. For example, if there is only one vacuum system for the four containers, equipment costs would be minimized. However, it may take a longer time to multitask and sterilize all four attachable/detachable containers 20.

With the system 100 of FIG. 34C, the attachable/detachable containers 20 may be sterilized independently of one another, in a synchronized manner, in an asynchonized manner, or in a multitasking manner with at least one vacuum source.

In each of the systems 100 illustrated in FIGS. 34A, 34B, and 34C, articles can be sterilized in attachable/detachable containers 20 without the need to place the articles in a large vacuum chamber. There are many advantages to sterilizing articles in attachable/detachable containers 20 which can be attached, sterilized, and detached from systems such as shown in FIGS. 34A, 34B, and 34C. First, an individual article to be sterilized can be placed into an attachable/detachable container 20, attached to a system 100, and can be sterilized at any time, rather than having to wait until enough equipment has been accumulated to make it worthwhile to sterilize a large load in a large sterilization chamber. Sterilizing an article in an attachable/detachable container 20 therefore provides flexibility in scheduling sterilization of individual articles.

Second, sterilizing an article in an attachable/detachable container 20 provides flexibility in varying the sterilization conditions. For example, if an article is to be sterilized with an unusual set of conditions, it may be sterilized in an attachable/detachable container 20 without having to sterilize an entire large load under the same set of conditions in a large sterilization chamber.

Third, the sterilized article is contained inside the attachable/detachable container 20 after being sterilized. The attachable/detachable container 20 with the sterilized article inside may be transported large distances inside the attachable/detachable container 20 without a need to be concerned that the article become accidentally contaminated by being exposed to bacteria. The sterilized article is protected from contamination by being contained in the attachable/detachable container 20.

Fourth, the attachable/detachable container 20 which is sterilized in the system 100 can be a nested container 20, as shown, for example, in FIGS. 28–31. The sterilized article is contained in the inner container 20A, which is in turn contained in the outer attachable/detachable container 20B. Because both the inside and the outside of the inner container 20A are sterile, the outer attachable/detachable container 20B can be transported to an area near to an operating room, the inner container 20A removed, and the sterile inner container 20A with the sterile article inside placed in a sterile area such as an operating room without having concerns about contaminating the sterile area with a nonsterilized container.

The various embodiments of attachable/detachable container 20 and the sterilization system shown in FIGS. 34A, 34B, and 34C therefore provide additional scheduling convenience and flexibility compared to conventional sterilization systems.

The sterilization system shown in FIGS. 34A, 34B, and 34C has been described in terms of introducing a liquid comprising vaporizable germicide into an attachable/detachable container 20. In an alternative embodiment, the attachable/detachable containers 20 and the sterilization systems such as shown in FIGS. 34A, 34B, and 34C can be used with germicide vapor rather than liquid.

In the embodiments where germicide vapor is used, the attachable/detachable container 20 can be any kind of container and is not necessarily diffusion restricted. If germicide vapor is used to sterilize articles in attachable/detachable containers 20, the process is as follows. An article to be sterilized is placed into the attachable/detachable container 20. The container 20 is attached to a vacuum source. The placing and attaching can be in either order. The attachable/detachable container 20 is evacuated, and germicide vapor is introduced into the attachable/detachable container 20, sterilizing the article and the inside of the attachable/detachable container 20. The container 20 with the sterilized article may be detached from the vacuum source. Plasma may optionally be introduced into the attachable/detachable container 20 before, during, and/or after the germicide vapor is introduced into the attachable/detachable container 20. If the plasma is introduced prior to introducing the germicide vapor, the plasma helps to dry the article to be sterilized and/or the interior of the attachable/detachable container 20. If the plasma is introduced during and/or after introducing the germicide vapor, the plasma helps to sterilize the article inside the attachable/detachable container 20 as well as the interior of the attachable/detachable container 20. The plasma also helps to remove the residual in the container. The source of germicide vapor can be liquid or solid.

Sterilization of articles in attachable/detachable containers 20 with germicide vapor rather than with liquid comprising vaporizable germicide has the same advantages as sterilization of articles in attachable/detachable containers 20 with liquid comprising vaporizable germicide. The advantages of sterilizing articles in attachable/detachable containers 20 include flexibility in scheduling, flexibility in varying sterilization conditions, the ability to transport sterilized articles in the attachable/detachable container without being concerned that the article be accidentally contaminated by bacteria, and the ability to sterilize an article in nested containers, where the outside of the inner container is sterile.

While the invention has been described in connection with preferred liquid sterilant solutions containing hydrogen peroxide, it will be appreciated by those having ordinary skill in the art that equivalent sterilization methods can be adapted for other sources of peroxide sterilants. In an alternative embodiment, a sterilant having a vapor pressure lower than that of water or other solvent in which the sterilant may be provided is used. For such sterilants, it is only important that the vapor pressure be lower than that of the solvent within the temperature ranges contemplated herein. In yet other embodiments, a solid source of peroxide sterilant may be utilized. Such liquid and solid sterilants can be adapted for the techniques described herein with only minor adjustments made for the differences in vapor pressure between hydrogen peroxide and such other sterilant, as can be readily determined by those having ordinary skill in the art. As long as the local vapor pressure at the site of the sterilant is below the vapor pressure of the sterilant, sterilization can be achieved substantially as described hereinabove.

Conclusion

Achieving rapid sterilization of lumened devices at low temperatures using low concentrations of sterilants has, until now, been exceedingly challenging. A superior method of sterilization has been discovered which overcomes the problems of the known methods. By pretreating articles to be sterilized or a diffusion-restricted environment containing the articles with a source of peroxide such as an aqueous solution of hydrogen peroxide prior to exposure to a vacuum, rapid sterilization can be achieved at low temperatures, without damage to the articles, without leaving toxic residues behind, and without the need to attach special vessels. The method of the present invention is efficient, nonhazardous, and inexpensive as well.

Methods are also provided for sterilizing articles in containers, including attachable/detachable containers and nested containers. Sterilizing methods in attachable/detachable containers provides flexibility in scheduling the sterilization as well as increasing the opportunities for transporting and utilizing the sterilized article in the attachable/detachable container without recontaminating the article.

What is claimed is:

1. A method for sterilizing an article in a diffusion restricted environment under reduced pressure, said method comprising:

placing said article in a container, wherein said container comprises at least one communication port and wherein said container is attachable to and detachable from a vacuum source through said communication port;

introducing a liquid solution comprising vaporizable germicide into said container;

attaching said container to said vacuum source through said communication port;

creating a diffusion restricted environment around the article to be sterilized, wherein the placing, introducing, attaching, and creating can occur in any order;

reducing the pressure in said container with said vacuum source through said communication port;

generating germicide vapor from said vaporizable germicide, wherein said germicide vapor diffuses from inside the container through the communication port to outside the container, thereby sterilizing said article in said container;

detaching said container from said vacuum source; and maintaining the sterility of said article.

2. The method of claim 1, further comprising venting said container through a vapor-permeable and microbe-impermeable filter.

3. The method of claim 1, wherein the pressure in said container is above or below atmospheric pressure when said container is detached from said vacuum source.

4. The method of claim 1, wherein said diffusion restricted environment is created with a diffusion restricted port.

5. The method of claim 1, wherein said introducing comprises delivery of said liquid solution comprising vaporizable germicide into said container via at least one method selected from the group consisting of injection, static soak, spray or flow-through with liquid or mist, and condensing vapor.

6. The method of claim 1, wherein said introducing further comprises contacting said article with said liquid solution comprising vaporizable germicide.

7. The method of claim 1, wherein said article comprises a diffusion restricted device.

8. The method of claim 1, wherein said vaporizable germicide comprises hydrogen peroxide.

9. The method of claim 1, wherein the pressure is reduced to below the vapor pressure of said vaporizable germicide during the reducing step.

10. The method of claim 1, wherein said communication port further comprises a valve.

11. The method of claim 10, wherein said valve is a hinged valve.

12. The method of claim 10, wherein said valve is a septum.

13. The method of claim 12, further comprising inserting a needlelike device through the septum.

14. The method of claim 1, further comprising attaching at least one additional container to said vacuum source.

15. The method of claim 14, wherein said container and said at least one additional container each contain an article to be sterilized, and wherein the articles to be sterilized can be sterilized independently, simultaneously, in a synchronized manner, in a asynchronized manner, or in a multitasking manner.

16. The method of claim 1, wherein the pressure is reduced to about 50 or less torr in said container with said vacuum source through said communication port.

17. The method of claim 16, wherein the pressure is reduced to about 25 or less torr in said container with said vacuum source through said communication port.

18. A method for sterilizing an article in a diffusion restricted environment under reduced pressure, said method comprising:

placing said article in a container, wherein said container comprises at least one communication port and wherein said container is attachable to and detachable from a vacuum source through said communication port;

introducing a liquid solution comprising vaporizable germicide into said container;

attaching said container to said vacuum source through said communication port;

creating a diffusion restricted environment around the article to be sterilized, wherein the placing, introducing, attaching, and creating can occur in any order, and wherein said diffusion restricted environment is created with a diffusion restricted port, wherein the diffusion restricted port is at least as diffusion restricted as a port having a length of 1.0 cm or a port having an open cross-sectional area of 63.62 mm$^2$ or a port having a length/cross-sectional area of 0.157 mm$^{-1}$;

reducing the pressure in said container with said vacuum source through said communication port;

generating germicide vapor from said vaporizable germicide, wherein said germicide vapor diffuses from inside the container through the communication port to outside the container, thereby sterilizing said article in said container;

detaching said container from said vacuum source; and maintaining the sterility of said article.

19. A method for sterilizing an article in a diffusion restricted environment under reduced pressure, said method comprising:

placing said article in a first container, wherein said first container comprises at least one communication port and wherein said first container is attachable to and detachable from a vacuum source through said communication port;

nesting a second container comprising at least one communication port inside said first container;

introducing a liquid solution comprising vaporizable germicide into said first container;

attaching said container to said vacuum source through said communication port;

creating a diffusion restricted environment around the article to be sterilized, wherein the placing, nesting, introducing, attaching, and creating can occur in any order;

reducing the pressure in said first container with said vacuum source through said communication port;

generating germicide vapor from said vaporizable germicide, wherein said germicide vapor diffuses from inside the first container through the communication port to outside the first container, thereby sterilizing said article in said first container;

detaching said first container from said vacuum source; and maintaining the sterility of said article.

20. The method of claim 19, wherein said second container further comprises a gas permeable and microbe-impermeable filter.

21. The method of claim 18, wherein said second container comprises a flexible pouch.

22. The method of claim 19, wherein a liquid solution comprising vaporizable germicide is in said second container before the reducing step.

23. The method of claim 19, wherein the pressure is reduced to a pressure below a vapor pressure of the vaporizable germicide.

24. A method for sterilizing an article in a container under reduced pressure, said method comprising:

placing said article in a container, wherein said container comprises at least one communication port and wherein said container is attachable to and detachable from a vacuum source through said communication port;

attaching said container to said vacuum source through said communication port, wherein said placing and said attaching can occur in either order;

reducing the pressure in said container with said vacuum source through said communication port;

introducing germicide vapor into said container though said communication port, thereby sterilizing said article;

detaching said container from said vacuum source; and maintaining the sterility of said article.

25. The method of claim 24, further comprising venting said container through a vapor-permeable and microbe-impermeable filter.

26. The method of claim 24, wherein the pressure in said container is above or below atmospheric pressure when said container is detached from said vacuum source.

27. The method of claim 24, wherein said germicide vapor comprises hydrogen peroxide.

28. The method of claim 24, wherein said communication port further comprises a valve.

29. The method of claim 24, further comprising attaching at least one additional container to said vacuum source.

30. The method of claim 29, wherein said container and said at least one additional container each contain an article to be sterilized, and wherein the articles to be sterilized can be sterilized independently, simultaneously, in a synchronized manner, in a asynchronized manner, or in a multitasking manner.

31. A method for sterilizing an article in a container under reduced pressure, said method comprising:

placing said article in a container, wherein said container comprises at least one communication port and wherein said container is attachable to and detachable from a vacuum source through said communication port;

nesting a second container comprising at least one communication port inside said container;

attaching said container to said vacuum source through said communication port, wherein said placing and said attaching can occur in either order;

reducing the pressure in said container with said vacuum source through said communication port;

introducing germicide vapor into said container through said communication port, thereby sterilizing said article;

detaching said container from said vacuum source; and maintaining the sterility of said article.

32. The method of claim 31, wherein said second container further comprises a gas permeable and microbe-impermeable filter.

33. The method of claim 31, wherein said second container comprises a flexible pouch.

* * * * *